(12) United States Patent
Grela et al.

(10) Patent No.: US 9,074,028 B2
(45) Date of Patent: Jul. 7, 2015

(54) COMPLEXES OF RUTHENUM, METHOD FOR THEIR PREPARATION, AND THEIR APPLICATION IN OLEFIN METATHESIS REACTIONS

(75) Inventors: Karol Leslaw Grela, Warsaw (PL); Michal Barbasiewicz, Warsaw (PL); Michal Michalak, Hajnówka (PL)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

(21) Appl. No.: 14/116,378

(22) PCT Filed: Jun. 4, 2012

(86) PCT No.: PCT/EP2012/060498
§ 371 (c)(1),
(2), (4) Date: Feb. 11, 2014

(87) PCT Pub. No.: WO2012/168183
PCT Pub. Date: Dec. 13, 2012

(65) Prior Publication Data
US 2014/0171607 A1 Jun. 19, 2014

(30) Foreign Application Priority Data
Jun. 6, 2011 (PL) .......................................... 395131

(51) Int. Cl.
| C07F 15/00 | (2006.01) |
| C08F 132/08 | (2006.01) |
| B01J 31/22 | (2006.01) |
| C07C 67/333 | (2006.01) |
| C07C 253/30 | (2006.01) |
| C07C 329/06 | (2006.01) |
| C07D 211/70 | (2006.01) |
| C07D 307/28 | (2006.01) |
| C07D 309/22 | (2006.01) |

(52) U.S. Cl.
CPC ........... *C08F 132/08* (2013.01); *B01J 31/2278* (2013.01); *C07C 67/333* (2013.01); *C07C 253/30* (2013.01); *C07C 329/06* (2013.01); *C07D 211/70* (2013.01); *C07D 307/28* (2013.01); *C07D 309/22* (2013.01); *C07F 15/0046* (2013.01); *B01J 2231/54* (2013.01); *B01J 2531/821* (2013.01)

(58) Field of Classification Search
CPC .................................................. C07F 15/0046
USPC ........................................ 556/136; 526/171
IPC ........................................ C08F 15/0046, 15/00
See application file for complete search history.

(56) References Cited

U.S. PATENT DOCUMENTS

| 8,501,975 B2 | 8/2013 | Kadyrov et al. |
| 8,716,488 B2 * | 5/2014 | Jensen et al. .................. 548/103 |
| 8,877,936 B2 | 11/2014 | Grubbs et al. |
| 2007/0043180 A1 | 2/2007 | Zhan |
| 2008/0275247 A1 | 11/2008 | Kadyrov et al. |

FOREIGN PATENT DOCUMENTS

| EP | 1914229 A1 | 4/2008 |
| WO | 2004/035596 A1 | 4/2004 |

OTHER PUBLICATIONS

Wang et al., Organometallics, 2012, 31, 1627-1634.*
Barbasiewicz, M.; Michalak, M.; Grela, K. Chem. Eur. J. 2012, 18 (45), 14237-14241.*
International Search Report for PCT/EP2012/060498: mailed Sep. 27, 2012.
Written Opinion for PCT/EP2012/060498: mailed Sep. 27, 2012.
Andrew Hejl, et al., "Latent Olefin Metathesis Catalysts Featuring Chelating Alkylidenes", American Chemical Society, 2006, pp. 6149-6154.
Michal Barbasiewicz et al.; "A New Family of Halogen-Chelated Hoveyda-Grubbs-Type Metathesis Catalysts"; Chem. Eur. J. 2012, 18, pp. 14237-14241.
Michal Barbasiewicz et al.; "A New Family of Halogen-Chelated Hoveyda-Grubbs-Type Metathesis Catalysts" Supporting Information zu Chem, Eur. J. 2012, 18, pp. 14237-14241.
Michal Barbasiewicz et al.; "Intriguing substituent effect in modified Hoveyda-Grubbs metathesis catalysts incorporating chelating iodo-benzylidene ligand t": Dalton Trans, 2013, 42, pp. 355-358.
Stefan Krehl et al.; "The catalytic performance of Ru-NHC alkylidene complexes: $PC_{y\,3}$ versus pyridine as the dissociating ligand"; Beilstein J. Org. Chem. 2010, 6, pp. 1188-1198.
Steven B, Garber et at; "Efficient and Recyclable Monomeric and Dendritic Ru-Based Metathesis Catalysts"; J. A. Chem. Soc. 2000, 122, pp. 8168-8179.

(Continued)

*Primary Examiner* — Rip A Lee
(74) *Attorney, Agent, or Firm* — Smith, Gambrell & Russell, LLP

(57) ABSTRACT

The present invention provides new ruthenium complexes of Formula (1), which contain a chelate ring created by a halogen atom X. The invention concerns also a method for the preparation of the new ruthenium complexes and their application in metathesis reactions.

(I)

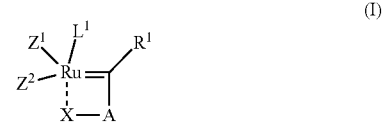

15 Claims, 3 Drawing Sheets

(56) References Cited

OTHER PUBLICATIONS

Figure 1:
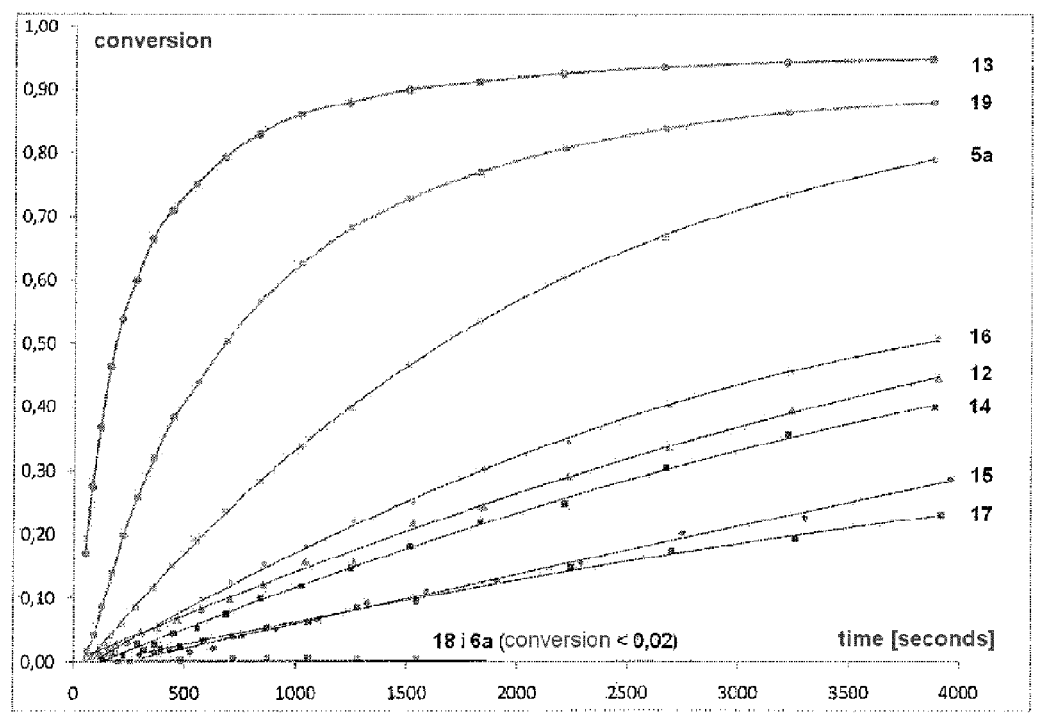

Simon Gessler et al.; "Synthesis and metathesis reactions of a phosphine-free dihydroimidazole carbene ruthenium complex"; Tetrahedron Lett, 2000, 41, pp. 9973-9976.

Prof. Dr. S. Blechert et al.; "Ein hochaktiver und luftstabbiler Rutheniumkomplex für die Olefinmetathese"; Angew. Chem. Int. Ed. 2002, 114, pp. 832-834.

Hideaki Wakamatsu et al.; "A New Highly Efficient Ruthenium Metathesis Catalyst"; Angew. Cremie Int. Ed. 2002, 114, pp. 2509-2511.

Oliver Schuster et. al.; "Beyond Conventional N-Heterocyclic Carbenes: Abnormal, Remote, and Other Classes of NHC Ligands with Reduced Heteroatom Stabilization": Chem. Rev. 2009, 109, pp. 3445-3478.

Kenichiro Sangu et al.; "Intermolecular Addition Reaction to Alkenes of Acylmolybdenum Complexes Generated by Oxidative Addition of Aryl or Alkenyl Halides with Molybdenum (0) Carbonyl Complexes", Synlett 2007, No. 6, pp. 929-933.

Steve V. Gagnier et al.; "Palladium-Catalyzed Carbonylative Cyclization of Unsaturated Aryl Iodides and Dienyl Triflates, Iodides, and Bromides to Indanones and 2-Cyclopentenones"; J. Am. Chem. Soc. 2003, 125, pp. 4804-4807.

\* cited by examiner

Catalytic activity in cyclisation of diethyl diallylmalonate for the catalysts of the invention ($^1$H-NMR methods; Kinetic profiles of the course of the reaction)

Kinetic profiles of the course of reactions with the catalyst of formula 18 at temperatures of 25, 40, and 55°C Kinetic profiles of the course of reactions with the catalyst of formula 15 at temperatures of 25, 40, and 55°C

COMPLEXES OF RUTHENUM, METHOD FOR THEIR PREPARATION, AND THEIR APPLICATION IN OLEFIN METATHESIS REACTIONS

The invention concerns new ruthenium complexes which act as (pre)catalysts, a method for their preparation, and their application in olefin metathesis reactions. This invention is used in organic synthesis in a broad sense.

In applications of olefin metathesis in organic synthesis, significant progress has been made in recent years. In the state of the art, a number of carbene complexes of ruthenium are known which act as (pre)catalysts and which display both high activity in various types of metathesis reaction and broad tolerance of functional groups. The above combination of properties makes this type of (pre)catalyst suitable in organic synthesis.

From the point of view of practical application, particularly on an industrial scale, it is highly desirable for such ruthenium complexes to be stable over a long period at an elevated temperature and to be stored and/or purified and/or used without a protective gas atmosphere.

Complexes of ruthenium with such properties are already known (see: J. Am. Chem. Soc. 2000, 122, 8168-8179; Tetrahedron Lett. 2000, 41, 9973-9976), although it has turned out that better stability is linked with reduced catalytic activity. This type of limitation was found in the case of the (pre)catalyst with formula 2, in which Mes denotes 2,4,6-trimethylphenyl (for a comparison of catalytic activity, see Angew. Chem. Int. Ed. 2002, 114, 832-834).

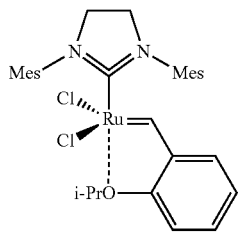

Formula 2

Then, (pre)catalysts are described with formulae 3 and 4, which show higher catalytic activity in comparison with the (pre)catalyst of formula 2.

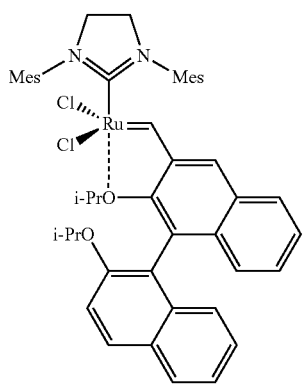

Formula 3

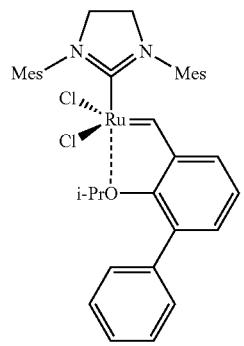

Formula 4

Catalysts 2, 3, and 4 contain an isopropoxyl group which chelates an atom of the metal. The higher activity of arrangements 3 and 4 is explained by the spatial hindrance introduced by the adjacency of the phenyl group or (substituted) naphthyl group in the ortho position in relation to the isopropoxyl group (see Angew. Chemie Int. Ed. 2002, 114, 832-834; Angew. Chemie Int. Ed. 2002, 114, 2509-2511).

Then, other catalysts are also described with formulae 5a, 5b, 6a, and 6b, in which Cy denotes cyclohexyl.

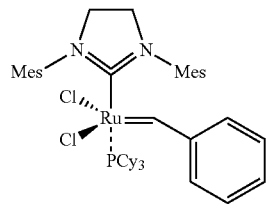

Formula 5a

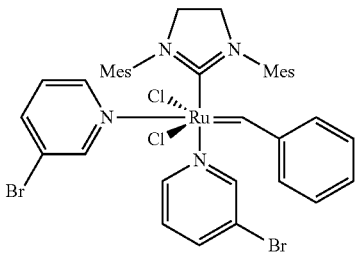

Formula 5b

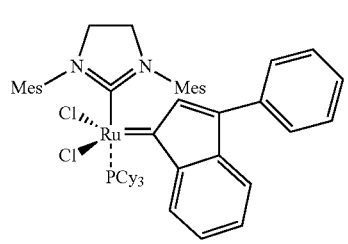

Formula 6a

Formula 6b

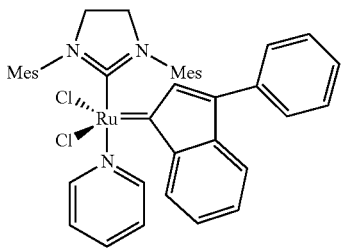

Unexpectedly, it was found that new complexes of ruthenium in accordance with the invention presented in formula 1:

Formula 1

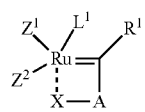

which contain a chelate ring created by a halogen atom are thermally stable and display good catalytic activity. In addition, these compounds display significant changes in activity as a function of temperature, which may be applied to control catalytic processes by changing the temperature of a reaction mixture. Known catalytic arrangements have not shown significant changes in catalytic activity as a function of temperature.

Complexes with formula 1, in accordance with the invention, are applied broadly. With a good result, numerous reactions can be carried out consisting not only in ring-closing metathesis but also in homometathesis, cross metathesis and metathesis of the alkene-alkyne (ene-yne) type, and ring-opening metathesis polymerisation (ROMP).

Thus, the synthesis of compounds that contain the double C=C bond and other functional groups, when the new catalysts in accordance with the invention are applied, proceeds with a very good result.

When such new complexes are applied in accordance with the invention as (pre)catalysts, the temperature of the reaction can be increased and/or, at the same time, the duration of the reaction can be increased in comparison with those conditions necessary when other known catalysts are used. In this way, there is an improvement both in yield and in the technical opportunity for carrying out the reaction.

One of the objects of the present invention is to provide new complexes of ruthenium with formula 1:

Formula 1

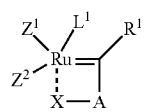

in which:
$L^1$ denotes an inert ligand;
$Z^1$ and $Z^2$ denote, independently, an anion ligand;
X denotes a halogen atom;
$R^1$ denotes an atom of hydrogen, a halogen atom, $C_1$-$C_{12}$ alkyl, $C_3$-$C_{12}$ cycloalkyl, $C_2$-$C_{12}$ alkenyl, $C_3$-$C_{12}$ cycloalkenyl $C_2$-$C_{12}$ alkynyl, $C_3$-$C_{12}$ cycloalkynyl, $C_1$-$C_{12}$ alkoxyl, $C_5$-$C_{20}$ aryl, $C_5$-$C_{20}$ heteroaryl, or 3-12-membered heterocycle;

A denotes a bivalent radical selected from a group comprising $C_1$-$C_{12}$ alkylene, $C_2$-$C_{12}$ alkenylene, $C_2$-$C_{12}$ alkynylene, $C_5$-$C_{20}$ arylene, or $C_5$-$C_{20}$ heteroarylene, in which the $C_1$-$C_{12}$ alkylene, the $C_2$-$C_{12}$ alkenylene, the $C_2$-$C_{12}$ alkynylene, the $C_5$-$C_{20}$ arylene, and the $C_5$-$C_{20}$ heteroarylene may be optionally substituted with at least one functional group $R^2$;

each $R^2$ functional group denotes, independently, a halogen atom, $C_1$-$C_{12}$ alkyl, $C_2$-$C_{12}$ alkenyl, $C_2$-$C_{12}$ alkynyl, —$OR^3$, —$SR^3$, —$S(O)_mR^3$, —$SO_2NR^3R^4$, —$S(O)_2OR^3$, —$NO_2$, —NO, —SCN, —$NR^3R^4$, —CN, —$C(O)R^3$, —$OC(O)R^3$, —$O(CR^3R^4)_nR^5$, —$NR^3C(O)R^4$, —$(CR^3R^4)_nC(O)OR^5$, —$(CR^3R^4)_nOR^5$, —$C(=NR^3)NR^4R^5$, —$NR^3C(O)NR^4R^5$, —$NR^3S(O)_pR^4$, —NC(=O) $R^3C(=O)R^4$, —$NR^3P(=O)R^4R^5$, —$NR^3As(=O)R^4R^5$, —$PR^3R^4$, —$POR^3R^4$, —$POR^3OR^4$, —$P(=O)R^3R^4$, —$P(=O)OR^3R^4$, —$P(=O)OR^3OR^4$, —$AsR^3R^4$, —$AsOR^3R^4$, —$AsOR^3OR^4$, —$As(=O)R^3R^4$, —$As(=O)OR^3R^4$, —$As(=O)OR^3OR^4$, —$NR^3$—$C(=NR^4)NR^5R^6$, —$C(=)R^3$, —$C(=O)OR^3$, —$C(=S)OR^3$, —$C(=O)SR^3$, —$C(=S)SR^3$, —$C(=S)NR^3R^4$, —$SiR^3R^4R^5$, —$SiOR^3R^4R^5$, —$SiOR^3OR^4R^5$, —$SiOR^3OR^4OR^5$, —$(CR^3R^4)_n$(3-12-membered heterocycle), —$(CR^3R^4)_n$($C_3$-$C_{12}$ cycloalkyl), —$(CR^3R^4)_n$($C_5$-$C_{20}$ aryl), —$(CR^3R^4)_n$(5-12-membered heteroaryl), —$(CR^3R^4)_nC(O)NR^5R^6$, or —$(CR^3R^4)_nC(O)R^5$;

and/or $R^2$ groups with adjacent atoms may bond together, creating $C_5$-$C_{20}$ aryl or 3-12-membered heterocycle; and/or $R^2$ groups with adjacent atoms may bond with the $R^1$ group, creating $C_5$-$C_{20}$ aryl, indenylene, heteroindenylene, 3-12-membered heterocycle, and polycyclic or heteropolycyclic arrangements, whilst the $C_5$-$C_{20}$ aryl, indenylene, heteroindenylene, 3-12-membered heterocycle, and polycyclic or heteropolycyclic arrangements may be substituted with at least one functional group selected from the group comprising a halogen atom, $C_1$-$C_{12}$ alkyl, $C_2$-$C_{12}$ alkenyl, $C_2$-$C_{12}$ alkynyl, —$OR^3$, —$SR^3$, —$S(O)_mR^3$, —$SO_2NR^3R^4$, —$S(O)_2OR^3$, —$NO_2$, —NO, —SCN, —$NR^3R^4$, —CN, —$C(O)R^3$, —$OC(O)R^3$, —$O(CR^3R^4)_nR^5$, —$NR^3C(O)R^4$, —$(CR^3R^4)_nC(O)OR^5$, —$(CR^3R^4)_nOR^5$, —$C(=NR^3)NR^4R^5$, —$NR^3C(O)NR^4R^5$, —$NR^3S(O)_pR^4$, —NC(=O)$R^3C(=O)$ $R^4$, —$NR^3P(=O)R^4R^5$, —$NR^3As(=O)R^4R^5$, —$PR^3R^4$, —$POR^3R^4$, —$POR^3OR^4$, —$P(=O)R^3R^4$, —$P(=O)OR^3R^4$, —$P(=O)OR^3OR^4$, —$AsR^3R^4$, —$AsOR^3R^4$, —$AsOR^3OR^4$, —$As(=O)R^3R^4$, —$As(=O)OR^3R^4$, —$As(=O)OR^3OR^4$, —$NR^3$—$C(=NR^4)NR^5R^6$, —$C(=O)R^3$, —$C(=O)OR^3$, —$C(=S)OR^3$, —$C(=O)SR^3$, —$C(=S)SR^3$, —$C(=S)NR^3R^4$, —$SiR^3R^4R^5$, —$SiOR^3R^4R^5$, —$SiOR^3OR^4R^5$, —$SiOR^3OR^4OR^5$, —$(CR^3R^4)_n$(3-12-membered heterocycle), —$(CR^3R^4)_n$($C_3$-$C_{12}$ cycloalkyl), —$(CR^3R^4)_n$($C_5$-$C_{20}$ aryl), —$(CR^3R^4)_n$(5-12-membered heteroaryl), —$(CR^3R^4)_nC(O)NR^5R^6$, or —$(CR^3R^4)_nC(O)R^5$;

each functional group $R^3$, $R^4$, $R^5$, and $R^6$ denotes, independently, an atom of hydrogen, a halogen atom, $C_1$-$C_{12}$ alkyl, $C_2$-$C_{12}$ alkenyl, $C_2$-$C_{12}$ alkynyl, $C_3$-$C_{12}$ cycloalkyl, $C_5$-$C_{20}$ aryl, 5-12-membered heterocycle;
each m denotes, independently, 0, 1, or 2;
each n denotes, independently, 0, 1, 2, 3, or 4;
each p denotes, independently, 1 or 2.

In one embodiment of the invention, $R^1$ in formula 1 denotes an atom of hydrogen, whilst anion ligands $Z^1$ and $Z^2$ denote, independently, a halogen atom, the group —CN, —SCN, —$OR^{13}$, —$SR^{13}$, —$O(C=O)R^{13}$, —$O(SO_2)R^{13}$, —$OSiR_3^{13}$, where $R^{13}$ denotes $C_1$-$C_{12}$ alkyl, $C_3$-$C_{12}$ cycloalkyl, $C_2$-$C_{12}$ alkenyl, or $C_5$-$C_{20}$ aryl, which may be optionally substituted with at least one $C_1$-$C_{12}$ alkyl, $C_1$-$C_{12}$ perhalogenalkyl, $C_1$-$C_{12}$ alkoxyl, or a halogen atom; and the inert ligand $L^1$ is selected from a group comprising —P($R^7$)$_3$, —P(O$R^7$)$_3$, or an N-heterocyclic carbene ligand with formula 7a, 7b, 7c, 7d, 7e, 7f, 7g, 7h, 7i, 7j, 7k, 7l, 7m, 7n, 7o, or 7p:

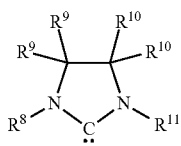

Formula 7a

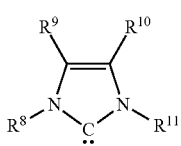

Formula 7b

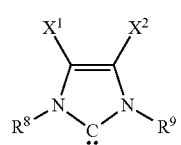

Formula 7c

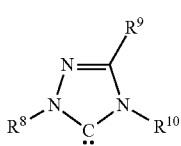

Formula 7d

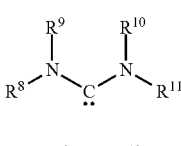

Formula 7e

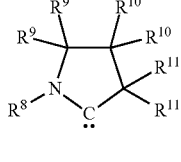

Formula 7f

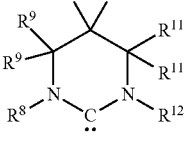

Formula 7g

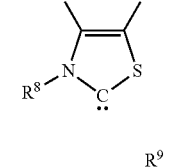

Formula 7h

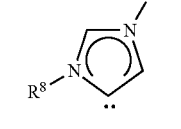

Formula 7i

-continued

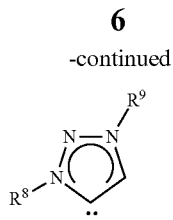

Formula 7j

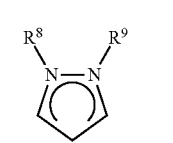

Formula 7k

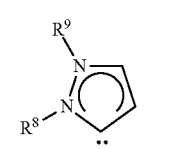

Formula 7l

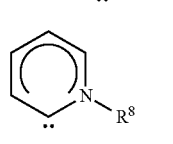

Formula 7m

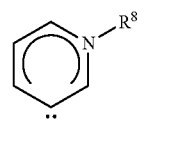

Formula 7n

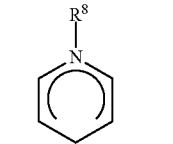

Formula 7o

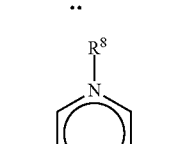

Formula 7p where:
each $R^2$ denotes, independently, $C_1$-$C_{12}$ alkyl, $C_3$-$C_{12}$ cycloalkyl, $C_5$-$C_{20}$ aryl, or 5-12-membered heteroaryl;
each $R^8$, $R^9$, $R^{10}$, $R^{11}$, and $R^{12}$ denote, independently, an atom of hydrogen, $C_1$-$C_{12}$ alkyl, $C_3$-$C_{12}$ cycloalkyl, $C_2$-$C_{12}$ alkenyl, or $C_5$-$C_{20}$ aryl, which may be optionally substituted with at least one $C_1$-$C_{12}$ alkyl, $C_1$-$C_{12}$ perhalogenalkyl, $C_1$-$C_{12}$ alkoxyl, or a halogen atom;
the groups $R^8$, $R^9$, $R^{10}$, $R^{11}$, and $R^{12}$ may optionally bond with each other and
$X^1$ and $X^2$ denote, independently, a halogen atom.
The carbene ligands may be coordinated classically, as in structures 7a-7h, or non-classically ('abnormal carbenes', see Chem. Rev. 2009, 109, 3445), as in structures 7i-7p.
In a further embodiment of the invention, the anion ligands $Z^1$ and $Z^2$ in formula 1 denote an atom of chlorine; and
X denotes an atom of bromine or iodine; and
A denotes 1,2-phenylene, 1,2-naphthylene, 2,3-naphthylene or 1,8-naphthylene, which may be substituted with at least one functional group selected from a group comprising —NO$_2$, —NMe$_2$; and the inert ligand $L^1$ denotes a ligand with formula 7a or 7b;

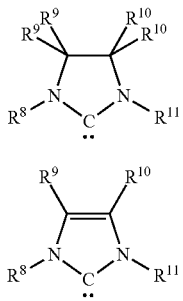

Formula 7a

Formula 7b in which the functional groups $R^8$, $R^9$, $R^{10}$, and $R^{11}$ may have the meaning described above.

In a still further embodiment of the invention, the anion ligands $Z^1$ and $Z^2$ in formula 1 denote an atom of chlorine; and X denotes an atom of bromine or iodine; and A denotes 1,2-phenylene, 1,2-naphthylene, 2,3-naphthylene or 1,8-naphthylene, which may be substituted with at least one functional group selected from a group comprising —OMe, Me and the inert ligand denotes a ligand with formula 7a or 7b as listed above.

An object of the invention is also to provide a method of preparing ruthenium complexes with formula 1, which comprises the reaction of the compound of formula 9

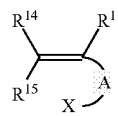

Formula 9 in which $R^{14}$ and $R^{15}$ denote, independently, an atom of hydrogen or the alkyl group $C_1$-$C_{12}$;

$R^1$ denotes hydrogen, a halogen atom, $C_1$-$C_{12}$ alkyl, $C_3$-$C_{12}$ cycloalkyl, $C_2$-$C_{12}$ alkenyl, $C_3$-$C_{12}$ cycloalkenyl, $C_2$-$C_{12}$ alkynyl, $C_3$-$C_{12}$ cycloalkynyl, $C_1$-$C_{12}$ alkoxyl, $C_5$-$C_{20}$ aryl, $C_5$-$C_{20}$ heteroaryl, or 3-12-membered heterocycle;

X denotes a halogen atom;

A denotes a bivalent radical selected from a group comprising $C_1$-$C_{12}$ alkylene, $C_2$-$C_{12}$ alkenylene, $C_2$-$C_{12}$ alkynylene, $C_5$-$C_{20}$ arylene, or $C_5$-$C_{20}$ heteroarylene, in which the $C_1$-$C_{12}$ alkylene, the $C_2$-$C_{12}$ alkenylene, the $C_2$-$C_{12}$ alkynylene, the $C_5$-$C_{20}$ arylene, and the $C_5$-$C_{20}$ heteroarylene may be optionally substituted with at least one functional group $R^2$;

each $R^2$ functional group denotes, independently, a halogen atom, $C_1$-$C_{12}$ alkyl, $C_2$-$C_{12}$ alkenyl, $C_2$-$C_{12}$ alkynyl, —$OR^3$, —$SR^3$, —$S(O)_mR^3$, —$SO_2NR^3R^4$, —$S(O)_2OR^3$, —$NO_2$, —NO, —SCN, —$NR^3R^4$, —CN, —$C(O)R^3$, —$OC(O)R^3$, —$O(CR^3R^4)_nR^5$, —$NR^3C(O)R^4$, —$(CR^3R^4)_nC(O)OR^5$, —$(CR^3R^4)_nOR^5$, —$C(=NR^3)NR^4R^5$, —$NR^3C(O)NR^4R^5$, —$NR^3S(O)_pR^4$, —$NC(=O)R^3C(=O)R^4$, —$NR^3P(=O)R^4R^5$, —$NR^3As(=O)R^4R^5$, —$PR^3R^4$, —$POR^3R^4$, —$POR^3OR^4$, —$P(=O)R^3R^4$, —$P(=O)OR^3R^4$, —$P(=O)OR^3OR^4$, —$AsR^3R^4$, —$AsOR^3R^4$, —$AsOR^3OR^4$, —$As(=O)R^3R^4$, —$As(=O)OR^3R^4$, —$NR^3$—$C(=NR^4)NR^5R^6$, —$C(=O)R^3$, —$C(=O)OR^3$, —$C(=S)OR^3$, —$C(=O)SR^3$, —$C(=S)SR^3$, —$C(=S)NR^3R^4$, —$SiR^3R^4R^5$, —$SiOR^3R^4R^5$, —$SiOR^3OR^4R^5$, —$SiOR^3OR^4OR^5$, —$(CR^3R^4)_n$(3-12-membered heterocycle), —$(CR^3R^4)_n(C_3$-$C_{12}$ cycloalkyl), —$(CR^3R^4)_n(C_5$-$C_{20}$ aryl), —$(CR^3R^4)_n$(5-12-membered heteroaryl), —$(CR^3R^4)_nC(O)NR^5R^6$, or —$(CR^3R^4)_nC(O)R^5$;

and/or $R^2$ groups with adjacent atoms may bond together, creating $C_5$-$C_{20}$ aryl or 3-12-membered heterocycle;

and/or $R^2$ groups with adjacent atoms may bond with the $R^1$ group, creating $C_5$-$C_{20}$ aryl, indenylene, heteroindenylene, 3-12-membered heterocycle, and polycyclic or heteropolycyclic arrangements, whilst the $C_5$-$C_{20}$ aryl, indenylene, heteroindenylene, 3-12-membered heterocycle, and polycyclic or heteropolycyclic arrangements may be substituted with at least one functional group selected from the group comprising a halogen atom, $C_1$-$C_{12}$ alkyl, $C_2$-$C_{12}$ alkenyl, $C_2$-$C_{12}$ alkynyl, —$OR^3$, —$SR^3$, —$S(O)_mR^3$, —$SO_2NR^3R^4$, —$S(O)_2OR^3$, —$NO_2$, —NO, —SCN, —$NR^3R^4$, —CN, —$C(O)R^3$, —$OC(O)R^3$, —$O(CR^3R^4)_nR^5$, —$NR^3C(O)R^4$, —$(CR^3R^4)_nC(O)OR^5$, —$(CR^3R^4)_nOR^5$, —$C(=NR^3)NR^4R^5$, —$NR^3C(O)NR^4R^5$, —$NR^3S(O)_pR^4$, —$NC(=O)R^3C(=O)R^4$, —$NR^3P(=O)R^4R^5$, —$NR^3As(=O)R^4R^5$, —$PR^3R^4$, —$POR^3R^4$, —$POR^3OR^4$, —$P(=O)R^3R^4$, —$P(=O)OR^3R^4$, —$P(=O)OR^3OR^4$, —$AsR^3R^4$, —$AsOR^3R^4$, —$AsOR^3OR^4$, —$As(=O)R^3R^4$, —$As(=O)OR^3R^4$, —$As(=O)OR^3OR^4$, —$NR^3$—$C(=NR^4)NR^5R^6$, —$C(=O)R^3$, —$C(=O)OR^3$, —$C(=S)OR^3$, —$C(=O)SR^3$, —$C(=S)SR^3$, —$C(=S)NR^3R^4$, —$SiR^3R^4R^5$, —$SiOR^3R^4R^5$, —$SiOR^3OR^4R^5$, —$SiOR^3OR^4OR^5$, —$(CR^3R^4)_n$(3-12-membered heterocycle), —$(CR^3R^4)_n(C_3$-$C_{12}$ cycloalkyl), —$(CR^3R^4)_n(C_5$-$C_{20}$ aryl), —$(CR^3R^4)_n$(5-12-membered heteroaryl), —$(CR^3R^4)_nC(O)NR^5R^6$, or —$(CR^3R^4)_nC(O)R^5$;

each functional group $R^3$, $R^4$, $R^5$, and $R^6$ denotes, independently, an atom of hydrogen, a halogen atom, $C_1$-$C_{12}$ alkyl, $C_2$-$C_{12}$ alkenyl, $C_2$-$C_{12}$ alkynyl, $C_3$-$C_{12}$ cycloalkyl, $C_5$-$C_{20}$ aryl, 5-12-membered heterocycle; each m denotes, independently, 0, 1, or 2;

each n denotes, independently, 0, 1, 2, 3, or 4;

each p denotes, independently, 1 or 2;

with a ruthenium carbene complex of formula 11a, 11b, 11c, or 11d:

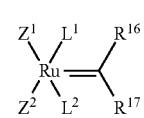

Formula 11a

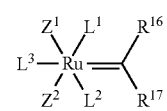

Formula 11b

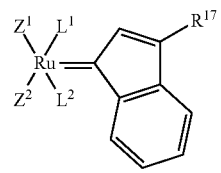

Formula 11c

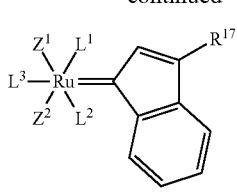

Formula 11d in which
$L^1$, $L^2$, and $L^3$ denote, independently, an inert ligand;
$Z^1$ and $Z^2$ denote, independently, an anion ligand;
$R^{16}$ has the same meaning as $R^1$ in formula 9;
$R^{17}$ denotes an atom of hydrogen, $C_5$-$C_{20}$ aryl, $C_5$-$C_{20}$ heteroaryl, vinyl, or allenyl.

Advantageously, the reaction between the compound of formula 9 and the ruthenium complex of formula 11a, 11b, 11c, or 11d is carried out in the presence of anhydrous halogen salts of copper(I) such as CuCl or CuBr, or in the presence of Brønsted acids such as $H_2SO_4$, HCl, $HNO_3$, $H_3PO_4$, sulphonated polymers (Nafion-H), or other acids bonded with a fixed substrate, in a solvent.

Advantageously, the reaction is carried out at a temperature in the range of 0-120° C.

Advantageously, the reaction is carried out in a chlorinated solvent or in aromatic hydrocarbons or in protic or aprotic solvents such as alcohol or ketone or in mixtures thereof.

Advantageously, the reaction is carried out in a solvent such as methylene chloride and/or toluene.

The invention also concerns the application and use of the ruthenium complexes defined in formula 1 as (pre)catalysts in metathesis reactions.

Advantageously, ruthenium complexes with formula 1 are used as (pre)catalysts in ring-opening metathesis reactions, homometathesis, cross-metathesis, alkene-alkyne (ene-yne) type metathesis, ring-closing metathesis and ROMP-type polymerisation reactions.

The term halogen atom denotes an element selected from F, Cl, Br, and I.

The term carbene denotes a molecule containing an inert atom of carbon with a valence number of two and two unpaired valence electrons. The term carbene also denotes carbene analogues in which the carbon atom is replaced with another chemical element such as boron, silicon, germanium, tin, lead, nitrogen, phosphorus, sulphur, selenium, and tellurium.

The term alkyl relates to a saturated, linear, or branched functional hydrocarbon group with an indicated number of atoms of carbon. Examples of an alkyl functional group are -methyl, -ethyl, -n-propyl, -n-butyl, -n-pentyl, -n-hexyl, -n-heptyl, -n-octyl, -n-nonyl, and -n-decyl. Representative branched —($C_1$-$C_{10}$) alkyls include -iso-propyl, -sec-butyl, -iso-butyl, -tert-butyl, -iso-pentyl, -neopentyl, -1-methylbutyl, -2-methylbutyl, -3-methylbutyl, -1,1-dimethylpropyl, -1,2-dimethylpropyl, -1-methylpentyl, -2-methylpentyl, -3-methylpentyl, -4-methylpentyl, -1-ethylbutyl, -2-ethylbutyl, -3-ethylbutyl, -1,1-dimethylbutyl, -1,2-dimethylbutyl, -1,3-dimethylbutyl, -2,2-dimethylbutyl, -2,3-dimethylbutyl, -3,3-dimethylbutyl, -1-methylhexyl, -2-methylhexyl, -3-methylhexyl, -4-methylhexyl, -5-methylhexyl, -1,2-dimethylpentyl, -1,3-dimethylpentyl, -1,2-dimethylhexyl, -1,3-dimethylhexyl, -3,3-dimethylhexyl, -1,2-dimethylheptyl, -1,3-dimethylheptyl, and -3,3-dimethylheptyl, and similar.

The term alkoxyl refers to an alkyl functional group as defined above connected using an oxygen atom.

The term perfluoroalkyl denotes an alkyl group as defined above in which all atoms of hydrogen are replaced with the same or different halogen atoms.

The term cycloalkyl refers to a saturated monocyclic or polycyclic functional hydrocarbon group with an indicated number of carbon atoms. Examples of a cycloalkyl functional group are -cyclopropyl, -cyclobutyl, -cyclopentyl, -cyclohexyl, -cycloheptyl, -cyclooctyl, -cyclononyl, -cyclodecyl, and similar.

The term alkenyl refers to a saturated, linear, or branched non-cyclic functional hydrocarbon group with an indicated number of atoms of carbon and containing at least one double carbon-carbon bond. Examples of an alkenyl functional group are -vinyl, -allyl, 1-butenyl -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and similar.

The term cycloalkenyl refers to a saturated monocyclic or polycyclic functional hydrocarbon group with an indicated number of atoms of carbon and containing at least one double carbon-carbon bond.

Examples of the cycloalkenyl functional group are -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, and similar.

The term alkynyl refers to a saturated, linear, or branched non-cyclic functional hydrocarbon group with an indicated number of atoms of carbon and containing at least one triple carbon-carbon bond. Examples of an alkynyl functional group are -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and similar.

The term cycloalkynyl refers to a saturated monocyclic or polycyclic functional hydrocarbon group with an indicated number of atoms of carbon and containing at least one triple carbon-carbon bond. Examples of a cycloalkynyl functional group are -cyclohexynyl, -cycloheptynyl, -cyclooctynyl, and similar.

The term aryl refers to an aromatic monocyclic or polycyclic functional hydrocarbon group with an indicated number of atoms of carbons. Examples of an aryl functional group are -phenyl, -tolyl, -xylyl, -naphthyl, and similar.

The term heteroaryl refers to an aromatic monocyclic or polycyclic functional hydrocarbon group with an indicated number of atoms of carbon with at least one atom of carbon replaced with a heteroatom selected from O, N, and S. Examples of a heteroaryl functional group are -furyl, -thienyl, -imidazolyl, -oxazolyl, -thiazolyl, -isoxazolyl, -triazolyl, -oxadiazolyl, -thiadiazolyl, -tetrazolyl, -pirydyl, -pyrimidyl, -triazynyl, -indolyl, -benzo[b]furyl, -benzo[b]thienyl, -indazolyl, -benzoimidazolyl, -azaindolyl, -chinolyl, -isochinolyl, -carbazolyl, and similar.

The term heterocycle refers to a saturated or partly saturated monocyclic or polycyclic functional hydrocarbon group, with an indicated number of atoms with at least one atom of carbon replaced with a heteroatom selected from O, N, and S. Examples of a heterocyclic functional group are -furyl, -thiophenyl, -pyrrolyl, -oxazolyl, -imidazolyl, -thiazolyl, -isoxazolyl, -pyrazolyl, -isothiazolyl, -triazynyl, -pyrrolidinolyl, -pyrrolidinyl, -hydrantoinyl, -oxyranil, -oxetanyl, -tetrahydrofuranyl, -tetrahydrothiophenyl, -quinolinyl, -isoquinolinyl, -chromonyl, -coumarinyl, -indolyl, -indolizinyl, -benzo[b]furanyl, -benzo[b]thiophenyl -indazolyl, -purinyl, -4H-quinolizinyl, -isoquinolyl, -quinolyl, -phthalazinyl, -naphthyridinyl, -carbazolyl, -β-carbolinyl, and similar.

The term inert ligand refers to a functional group without a charge capable of coordinating with the metallic centre (the ruthenium atom). Examples of such ligands are: amines, phosphines and oxides thereof, aryl and alkyl phosphoranes and phosphorines, arsines and oxides thereof, ethers, aryl and alkyl sulphides, coordinated hydrocarbons, and aryl and alkyl halides.

The term indenylene refers to an unsaturated functional hydrocarbon with an indene skeleton (benzocyclopentadiene).

The term heteroindenylene refers to an indenylene functional group, defined above, in which at least one atom of carbon has been replaced with a heteroatom from a group comprising: nitrogen, oxygen, and sulphur.

The term anion ligand refers to a functional group capable of coordination with the metallic centre (the ruthenium atom) with a charge capable of partial or full compensation of the metallic centre charge. Examples of such ligands may be: fluoride, chloride, bromide, iodide, cyanide, cyanate, and thiocyanate, carboxylic acid anions, alcohol anions, phenol anions, thiol and thiophenol anions, hydrocarbon anions with a delocalised charge (e.g. cyclopentadiene), (organo)sulphuric and (organo)phosphoric acid anions and their esters (e.g. alkyl sulphonic and aryl sulphonic acid anions, alkyl phosphoric and aryl phosphoric acid anions, sulphuric acid alkyl and aryl ester anions, phosphoric acid alkyl and aryl ester anions, alkyl phosphoric and aryl phosphoric acid alkyl and aryl ester anions). An anion ligand may have a group $L^1$, $L^2$, or $L^3$ linked like a catechol anion, an acetylacetone anion, or a salicylic aldehyde anion. Anion ligands ($Z^1$ and $Z^2$) and inert ligands ($L^1$, $L^2$, and $L^3$) may be linked with each other, creating polydentate ligands, e.g.: the bidentate ligand ($Z^1$, $Z^2$), the tridentate ligand ($Z^1$, $Z^2$, $L^1$), the tetradentate ligand ($Z^1$, $Z^2$, $L^1$, $L^2$), the bidentate ligand ($Z^1$, $L^1$), the tridentate ligand ($Z^1$, $L^1$, $L^2$), the tetradentate ligand ($Z^1$, $L^1$, $L^2$, $L^3$), the bidentate ligand ($L^1$, $L^2$), and the tridentate ligand ($L^1$, $L^2$, $L^3$). Examples of such ligands are: catechol anion, acetylacetone anion, and salicylic aldehyde anion.

The stages of synthesis which are generally used in producing ligands with formula 9 are presented in general in Diagram I, in accordance with which the synthesis of the compounds with formulae 21, 23, and 25 is carried out (Examples I-III).

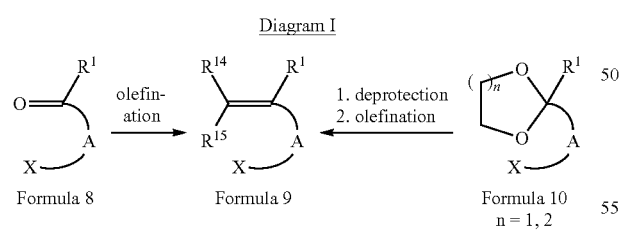

Formula 8   Formula 9   Formula 10 n = 1, 2

The olefination reaction of substituted aromatic and heteroaromatic halogen aldehyde derivatives with formula 8, where $R^1$ has the meaning given above, is advantageously carried out in accordance with Tebbe's method with Tebbe's titanium reagent or in accordance with Wittig's method with Wittig's reagent, or in accordance with Peterson's method. The reaction is carried out in solvents such as alcohol and glycol ethers or cyclic ethers, advantageously THF, aromatic and aliphatic hydrocarbons, and mixtures of all of the above. Compounds with the general formula 9 are also beneficially obtained from the protected aldehyde 10 without generation and purification of the halogen aldehyde with the general formula 8 (Diagram I, experimental data Examples I-III).

In the method in accordance with the invention, the complex with formula 1 is obtained as presented in Diagram II (for experimental data, see Examples IV-XI) in a reaction between the substituted compound with formula 9 and the ruthenium complex 11a, 11b, 11c, or 11d, where the functional group has the meaning given above, possibly in the presence of an anhydrous halogen salt of copper(I), such as CuCl or CuBr. The reaction is carried out advantageously in chlorinated solvents, e.g. methylene chloride, or in aromatic hydrocarbons, or in mixtures thereof, over 1-24 hours at a temperature of 0-120° C. Furthermore, protic and aprotic solvents may be used, such as alcohols or ketones. The reaction may be carried out also in the presence of Brønsted acids such as $H_2SO_4$, HCl, $HNO_3$, $H_3PO_4$, sulphonated polymers (Nafion-H), or other acids bonded with a fixed substrate, in the solvent described above.

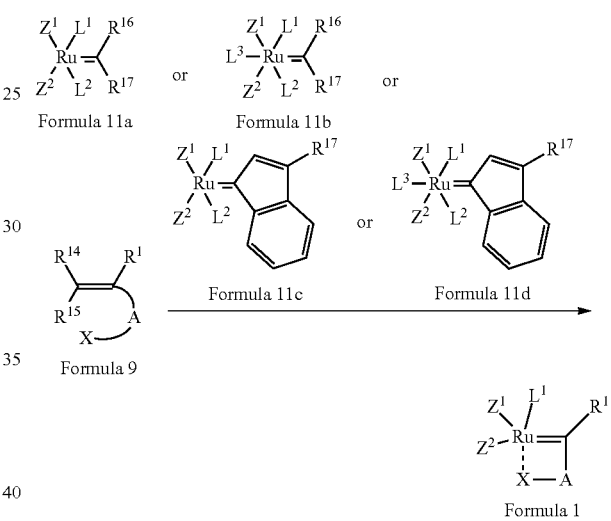

The examples above explain the production and use of the new complexes. The comparative examples with the use of known complexes confirm that the complexes in accordance with the invention of formula 1 are thermally more stable than complexes known from the state of the art and furthermore display higher catalytic activity.

EXAMPLE I

Synthesis of a Ligand with Formula 23 (in Accordance with Diagram I)

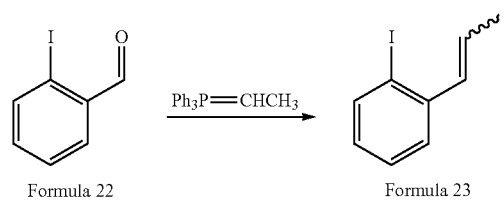

Formula 22   Formula 23

1-iodo-2-(prop-1-enyl)benzene. To the suspension of ethyl triphenyl phosphonium bromide (6.72 g, 18.3 mmol) in THF (30 ml), a solution is added by drops of tert-amylate (8.5 ml, 14.5 mmol, 1.7 M solution in toluene) at room temperature. After 1 hour, the reaction mixture is cooled to a temperature of 0° C., an aldehyde solution with formula 22 is added (2.80 g, 12.1 mmol) in THF (10 ml), the cooling bath is removed, and the mixing is continued for 3 hours at room temperature. This is followed by the addition of water (0.5 ml), dilution with n-hexane (30 ml), drying using $MgSG_4$, and the solvent is evaporated at reduced pressure. The residue is chromatographed on silica gel (cyclohexane), obtaining a styrene derivative with formula 23 in the form of a colourless oil as a mixture of isomers E:Z=1.83:1 (2.69 g, 91%).

$^1$H NMR (200 MHz): 7.80-7.70 (m, 1H), 7.45-7.18 (m, 1H), 6.96-6.78 (m, 1H), 6.62-6.26 (m, 1H), 1.90 (dd, J=6.6 Hz, 1.6 Hz, 0.35×3H), 1.73 (dd, J=7.0 Hz, 1.6 Hz, 0.65×1H).
$^{13}$C NMR (50 MHz): 140.8, 139.3, 139.0, 134.7, 133.7, 129.8, 129.0, 128.3, 128.2, 128.2, 127.7, 127.6, 126.3, 100.2, 99.2, 18.6, 14.1.

The compound described in Synlett 2007, 929-933, and J. Am. Chem. Soc. 2003, 125, 4804-4807 without spectral data.

EXAMPLE II

Synthesis of a Ligand with Formula 21 (in Accordance with Diagram I)

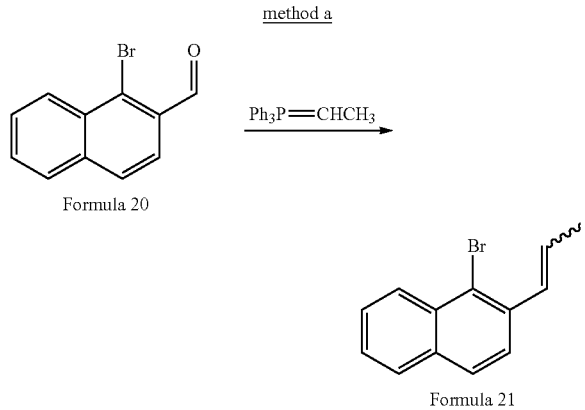

1-bromo-2-(prop-1-enyl)naphthalene. To the suspension of ethyl triphenyl phosphonium bromide (3.72 g, 10.0 mmol) in anhydrous THF (8 ml), a solution is added by drops of potassium tert-amylate (5.5 ml, 9.3 mmol, 1.7 M solution in toluene) using a syringe at room temperature. After 1 hour, the reaction mixture is cooled to a temperature of 0° C., a solution is added of aldehyde with formula 20 (1.68 g, 7.16 mmol), the cooling bath is removed, and mixing is carried out for 3 hours at room temperature. Then, the reaction mixture is diluted with cyclohexane (30 ml), the sediment is filtered off, and the solvent is evaporated at reduced pressure. The residue is chromatographed on silica gel (cyclohexane), obtaining a naphthalene derivative with formula 21 in the form of an oil as a mixture of isomers E:Z=1.82:1 (1.66 g, 94%).

$^1$H NMR (200 MHz): 8.44-8.32 (m, 1H), 7.88-7.40 (m, 5H), 7.18-7.02 (m, 0.65×1H), 6.76 (dd, J=11.4, 1.6 Hz, 0.35× 1H), 6.35 (dq, J=15.8, 6.6 Hz, 0.65×1H), 6.00 (dq, J=11.4, 7.0 Hz, 0.35×1H), 2.03 (dd, J=6.6, 1.6 Hz, 0.65×3H), 1.88-1.82 (m, 0.35×3H).

$^{13}$C NMR (50 MHz): 135.7, 135.1, 133.5, 133.3, 132.6, 131.0, 130.6, 129.7, 128.1, 128.0, 127.9, 127.6, 127.5, 127.4, 127.3, 127.2, 126.8, 126.2, 126.1, 124.2, 123.6, 122.5, 18.9, 14.6.

HR MS was calculated for $C_{13}H_{11}Br$: 246.0044. Found: 246.0054.

Spectroscopy data in accordance with the literature: Daiichi Sankyo Company, Ltd. Patent application: EP 1 914 229 A1, 2008.

EXAMPLE III

Synthesis of a Ligand with Formula 25 (in Accordance with Diagram I)

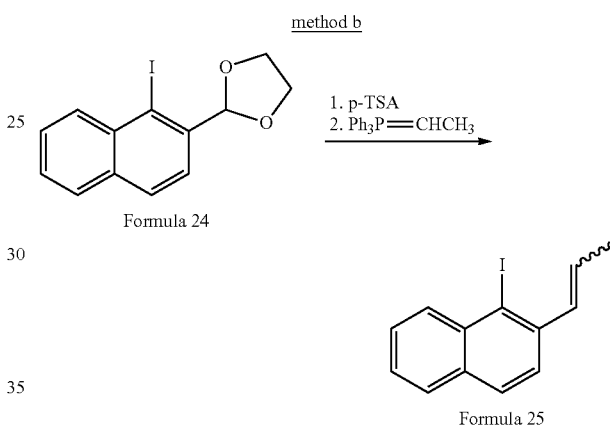

1-Iodo-2-(prop-1-enyl)naphthalene. To the solution of ketal with formula 24 (4.63 g, 14.3 mmol) in a mixture of 1,4-dioxane (40 ml) and water (5 ml), p-toluenesulfonic acid (1.36 g, 7.15 mmol) is added and mixed for 16 hours at room temperature. Then, the reaction mixture is diluted with water (100 ml) and a saturated hydrous solution $K_2CO_3$ (10 ml), and EtOAc (3×20 ml) is extracted. The combined organic extracts are rinsed with a saturated solution of NaCl (2×30 ml) and dried using $MgSO_4$, and the solvent is evaporated at reduced pressure, obtaining aldehyde in the form of a yellow solid (3.99 g, 99%). The aldehyde obtained is used for the subsequent reaction without further purification.

To the suspension of ethyl triphenyl phosphonium bromide (5.69 g, 15.3 mmol) in anhydrous THF (30 ml), a solution is added by drops of potassium tert-amylate (8.7 ml, 14.7 mmol, 1.7 M solution in toluene) using a syringe at room temperature. After 1 hour, the reaction mixture is cooled to a temperature of 0° C., the solution of crude aldehyde previously obtained is added (3.32 g, 11.79 mmol) in THF (10 ml), and mixing is continued for hours at room temperature. Then, water (1 ml) is added, and dilution takes place with n-hexane (30 ml). The sediment created is filtered, and the residue is chromatographed on silica gel (cyclohexane), obtaining naphthalene derivative with formula 25 in the form of a yellow oil (3.12 g, 90%).

EXAMPLE IV

Synthesis of a Catalyst with Formula 12, in which Mes Denotes 2,4,6-trimethylphenyl (in Accordance with Diagram II)

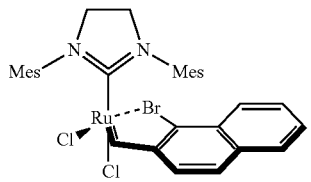

Formula 12

Procedure A: using a protective atmosphere of argon, in a Schlenk flask are placed anhydrous CuCl (0.0208 g, 0.21 mmol, 1.05 equivalent), bromonaphthalene equivalent with formula 21 (0.0544 g, 0.22 mmol, 1.10 equivalent), dry, deoxygenated $CH_2Cl_2$ (10 ml), and solid carbene ruthenium complex with formula 5a (in which Mes denotes 2,4,6-trimethylphenyl, and Cy denotes cyclohexyl):

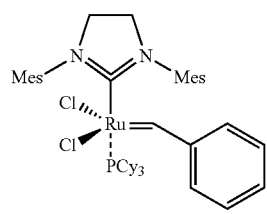

Formula 5a ('Grubbs' II generation catalyst, 0.170 g, 0.20 mmol) in the sequence indicated. The suspension obtained is mixed at boiling point for 2 hours. From this moment, all subsequent operations are carried out without the use of a protective atmosphere of argon. The reaction mixture is concentrated in a rotary evaporator, and the residue obtained is chromatographed on silica gel (20 ml), using as eluent 20% ethyl acetate in $CH_2Cl_2$. Then, solvents are evaporated at reduced pressure, obtaining a catalyst with Formula 12 as a green solid (0.094 g, 68%).

Procedure B: using a protective atmosphere of argon, in a Schlenk flask are placed bromonaphthalene derivative with formula 21 (0.741 g, 3.0 mmol, 1.10 equivalent), dry, deoxygenated toluene (67 ml), and solid carbene ruthenium complex with formula 6b:

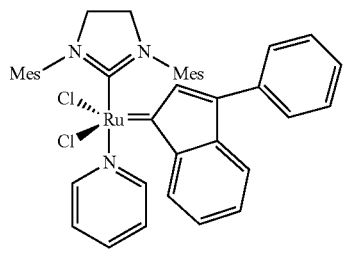

Formula 6b ('catalyst M31', Umicore AG & Co KG, 1.52 g, 2.0 mmol) in the sequence indicated. The suspension obtained is mixed at a temperature of 80° C. for 2 hours. From that moment, all operations are carried out without the use of a protective atmosphere of argon. The product suspension obtained is filtered off using a Büchner funnel, rinsed with n-pentane (2×8 ml), and dried for hours, obtaining a catalyst with formula 12 as a dark green solid (1.05 g, 75%).

$^1$H NMR (500 MHz, $CD_2Cl_2$): 17.97 (s, 1H), 8.22 (dd, J=8.5, 1.0 Hz, 1H), 7.89 (d, J=8.0 Hz, 1H), 7.75 (ddd, J=8.5, 7.0, 1.5 Hz, 1H), 7.72 (d, J=8.0 Hz, 1H), 7.64 (ddd, J=8.5, 7.0, 1.5 Hz, 1H), 7.18 (2 s ovl, 2H), 7.10 (d, J=8.5 Hz, 1H), 6.97 (s, 1H), 5.73 (s, 1H), 4.26-4.19 (m, 1H), 4.12-4.04 (m, 2H), 3.87-3.80 (m, 1H), 2.64 (s, 3H), 2.53 (s, 3H), 2.46 (s, 3H), 2.43 (s, 3H), 2.17 (s, 3H), 1.34 (s, 3H).

$^{13}$C NMR (125 MHz, $CD_2Cl_2$): 278.1, 214.1, 149.4, 141.0, 140.6, 139.1, 138.1, 137.1, 135.7, 135.4, 134.4, 131.9, 131.7, 131.3, 130.4, 130.0, 129.7, 129.5, 129.4, 129.3, 128.3, 127.4, 126.7, 124.8, 52.0, 51.9, 21.6, 21.2, 20.4, 19.5, 18.8, 17.3.

Elemental analysis for $C_{32}H_{34}Cl_2BrN_2Ru$: calculated: C 55.02, H 4.91, N 4.01. Found: C 56.11, H 5.16, N 3.88.

EXAMPLE V

Synthesis of a Catalyst with Formula 14 (in Accordance with Diagram II)

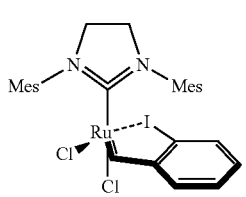

Formula 14

Using a protective atmosphere of argon, in a Schlenk flask are placed iodostyrene with formula 23 (0.549 g, 2.25 mmol, 1.10 equivalent), dry, deoxygenated toluene (50 ml) and solid carbene ruthenium complex with formula 6b ('catalyst M31', Umicore AG & Co KG, 1.14 g, 1.50 mmol), in the sequence indicated. The suspension obtained is mixed at a temperature of 80° C. for 2 hours. From this moment, all subsequent operations are carried out in air, without the use of a protective atmosphere of argon. The reaction mixture is cooled to room temperature, diluted with n-pentane (50 ml), filtered off using a Büchner funnel, rinsed with n-pentane (2×4 ml), and dried for 16 hours, obtaining [a catalyst] with formula 14 as a dark green solid (0.823 g, 70%, solvate with toluene 1:1, in accordance with $^1$H NMR).

$^1$H NMR (500 MHz, $CD_2Cl_2$): 18.06 (d, J=1.0 Hz, 1H), 7.61-7.57 (m, 1H), 7.35 (ddd, J=9.0, 7.5, 1.5 Hz, 1H), 7.29 (ddd, J=8.5, 7.0, 1.0 Hz, 1H), 7.17 (s, 1H), 7.04 (s, 1H), 6.94 (s, 1H), 6.91 (dd, J=7.2, 3.7 Hz, 1H), 6.01 (s, 1H), 4.25-4.17 (m, 1H), 4.10-3.96 (m, 2H), 3.91-3.84 (m, 1H), 2.71 (s, 3H), 2.50 (s, 3H), 2.41 (s, 3H), 2.38 (s, 3H), 2.16 (s, 3H), 1.62 (s, 3H). Signals of toluene omitted.

$^{13}$C NMR (125 MHz, $CD_2Cl_2$): 281.7, 214.7, 157.7, 141.0, 140.5, 139.0, 138.2, 136.5, 136.0, 135.7, 134.3, 132.0, 131.4, 130.8, 130.3, 130.0, 129.5, 129.3, 128.1, 100.7, 52.1, 51.8, 21.5, 21.2, 20.6, 20.3, 19.0, 18.2. Signals of toluene omitted.

Elemental analysis for $C_{35}H_{40}Cl_2IN_2Ru$: calculated: C 53.38, H 5.12, N 3.56. Found: C 53.32, H 5.10, N 3.90.

EXAMPLE VI

Synthesis of a Catalyst with Formula 15 (in Accordance with Diagram II)

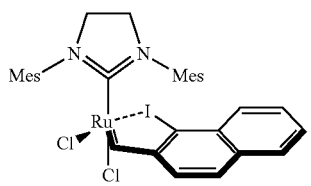

Formula 15

Procedure A: using a protective atmosphere of argon, in a Schlenk flask are placed iodonaphthalene derivative with formula 25 (0.706 g, 2.4 mmol, 1.10 equivalent), dry, deoxygenated toluene (50 ml), and solid carbene ruthenium complex with formula 6b ('M31 catalyst', Umicore AG & Co KG, 1.52 g, 2.0 mmol), in the sequence indicated. The suspension obtained is mixed at a temperature of 80° C. for 45 minutes. From this moment, all operations are carried out in air, without the use of a protective atmosphere of argon. The reaction mixture is cooled to room temperature, diluted with n-pentane (50 ml), filtered off using a Büchner funnel, rinsed with n-pentane (2×20 ml), and dried for 16 hours, obtaining a catalyst with formula 15 as a dark green solid (1.385 g, 93%).

Procedure B: using a protective atmosphere of argon, in a Schlenk flask are placed anhydrous CuCl (0.0156 mg, 0.158 mmol, 1.05 equivalent), iodonaphthalene derivative with formula 25 (0.0485 g, 0.165 mmol, 1.10 equivalent), dry, deoxygenated $CH_2Cl_2$ (7.5 ml), and solid carbene ruthenium complex with formula 5a:

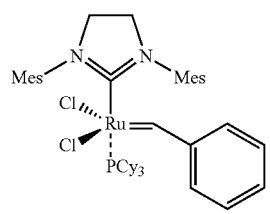

Formula 5a ('Grubbs II generation catalyst', 0.127 g, 0.150 mmol), in the sequence indicated. The suspension obtained is mixed at boiling point for 10 minutes. From this moment, all operations are carried out in air, without the use of a protective atmosphere of argon. The reaction mixture is concentrated in a rotary evaporator, and the residue obtained is chromatographed on silica gel (20 ml), using, as eluent, 10% ethyl acetate in $CH_2Cl_2$. Then, the solvents are evaporated at reduced pressure, obtaining a catalyst with formula 15 as an olive green solid (0.0923 g, 83%).

$^1$H NMR (500 MHz, $CD_2Cl_2$): 18.26 (s, =CH, 1H), 7.97 (d, J=8.0 Hz, 1H), 7.82 (d, J=8.0 Hz, 1H), 7.76-7.71 (m, 2H), 7.63-7.58 (m, 1H), 7.19 (s, 1H), 7.09 (s, 1H), 6.97 (s, 1H), 6.96 (d, J=8.0 Hz, 1H), 5.76 (s, 1H), 4.26-4.17 (m, 1H), 4.10-3.95 (m, 2H), 3.88-3.80 (m, 1H), 2.74 (s, 3H), 2.54 (s, 3H), 2.48 (s, 3H), 2.41 (s, 3H), 2.16 (s, 3H), 1.39 (s, 3H).

$^{13}$C NMR (125 MHz, $CD_2Cl_2$): 281.2, 214.3, 156.3, 141.0, 140.5, 139.0, 138.2, 136.5, 135.8, 135.5, 134.6, 133.9, 132.1, 131.4, 130.9, 130.4, 130.1, 129.8, 129.5, 129.4, 128.4, 126.4, 105.8, 52.2, 51.8, 21.5, 21.2, 20.6, 19.1, 18.1.

Elemental analysis for $C_{32}H_{34}Cl_2IN_2Ru$: calculated: C 51.55, H 4.60, N 3.76. Found: C 52.26, H 4.61, N 3.59.

EXAMPLE VII

Synthesis of a Catalyst with Formula 17 (in Accordance with Diagram II)

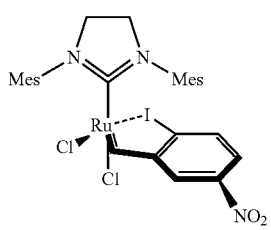

Formula 17

Procedure: using a protective atmosphere of argon, in a Schlenk flask are placed iodostyrene derivative with formula 28 (0.433 g, 1.5 mmol):

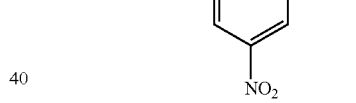

Formula 28 sand dry, deoxygenated toluene (20 ml), and solid, carbene complex of ruthenium with formula 6b ('M31 catalyst', Umicore AG & Co KG, 0.761 g, 1.0 mmol), in the sequence indicated. The suspension obtained is mixed at a temperature of 80° C. for 1 hour. From this moment, all operations are carried out in air, without the use of a protective atmosphere of argon. The reaction mixture is cooled to room temperature, diluted with n-pentane (20 ml), filtered using a Schott filter, rinsed with n-pentane (3×10 ml), and dried under pressure, obtaining a compound with formula 17 as a light green solid (0.659 g, 79%, solvate with toluene 1:1 in accordance with $^1$H NMR).

$^1$H NMR (200 MHz, $CD_2Cl_2$): 18.11 (d, J=1.0 Hz, =CH, 1H), 8.19, (dd, J=8.5, 2.5 Hz, 1H), 7.79 (dd, J=8.5, 1.0 Hz, 1H), 7.72 (d, J=2.5 Hz, 1H), 7.27-7.12 (m, 1H+toluene), 7.05 (s, 1H), 7.02 (s, 1H), 6.05 (s, 1H), 4.27-4.20 (m, 1H), 4.13-3.97 (m, 2H), 3.93-3.85 (m, 1H), 2.69 (s, 3H), 2.50 (s, 3H), 2.42 (s, 3H), 2.39 (s, 3H), 2.34 (s, toluene), 2.08 (s, 3H), 1.61 (s, 3H).

$^{13}$C NMR (125 MHz, $CD_2Cl_2$): 276.9, 212.9, 157.7, 149.5, 141.2, 140.5, 139.8, 138.4, 136.2, 135.8, 135.6, 134.7, 131.39, 131.37, 130.22, 130.20, 129.4, 129.0, 128.6, 125.6, 123.5, 120.9, 107.6, 52.0, 51.7, 21.5, 21.4, 20.7, 20.4, 20.1, 18.8, 18.1. Signals of toluene were omitted.

EXAMPLE VIII

Synthesis of a Catalyst with Formula 18 (in Accordance with Diagram II)

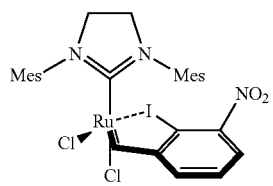

Formula 18

Procedure: using a protective atmosphere of argon, in a Schlenk flask are placed an iodostyrene derivative with formula 29 (0.453 g, 1.56 mmol):

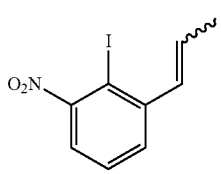

Formula 29 dry, deoxygenated toluene (20 ml) and solid carbene ruthenium complex with formula 6b ('catalyst M31', Umicore AG & Co KG, 0.787 g, 1.04 mmol). The suspension obtained is mixed at a temperature of 80° C. for 1 hour. From this moment, all operations are carried out in air, without the use of a protective atmosphere of argon. The reaction mixture is cooled to room temperature, diluted with n-pentane (20 ml), filtered using a Schott filter, rinsed with n-pentane (3×15 ml), and dried under pressure, obtaining a catalyst with formula 18 as a bronze-coloured solid (0.745 g, 86%, solvate with toluene 1:1, in accordance with $^1$H NMR).

$^1$H NMR (500 MHz, CD$_2$Cl$_2$): 18.12 (s, =CH, 1H), 8.41 (dd, J=8.0, 1.5 Hz, 1H), 7.52 (dd, J=8.0, 7.5 Hz, 1H), 7.26-7.12 (m, 2H +toluene), 7.08 (s, 1H), 6.96 (s, 1H), 5.97 (s, 1H), 4.25-4.18 (m, 1H), 4.11-3.95 (m, 2H), 3.92-3.84 (m, 1H), 2.69 (s, 3H), 2.51 (s, 3H), 2.47 (s, 3H), 2.39 (s, 3H), 2.34 (s, toluene), 2.14 (s, 3H), 1.62 (s, 3H).

$^{13}$C NMR (125 MHz, CD$_2$Cl$_2$): 279.0, 212.9, 158.7, 150.7, 141.1, 140.4, 139.1, 138.4, 138.3, 136.1, 135.7, 135.5, 132.2, 131.4, 131.3, 131.1, 130.22, 130.17, 129.4, 129.1, 128.6, 125.6, 125.4, 93.1, 51.9, 51.8, 21.4, 21.1, 20.4, 20.1, 18.8, 18.2. Signals of toluene are omitted.

EXAMPLE IX

Synthesis of a Catalyst with Formula 13 (in Accordance with Diagram II)

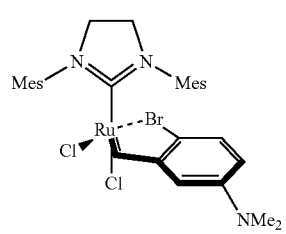

formula 13

Procedure: using a protective atmosphere of argon, in a Schlenk flask are placed a bromostyrene derivative with formula 26 (0.371 g, 1.55 mmol):

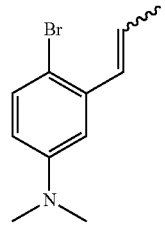

Formula 26 dry, deoxygenated toluene (20 ml), and solid carbene ruthenium complex with formula 6b ('catalyst M31', Umicore AG & Co KG, 0.780 g, 1.03 mmol), in the sequence indicated. The suspension obtained is mixed at a temperature of 80° C. for 30 minutes. From that moment, all operations are carried out in air, without the use of a protective atmosphere of argon. The reaction mixture is cooled to room temperature, diluted with n-pentane (20 ml), filtered using a Schott filter, rinsed with n-pentane (2×10 ml), and dried under pressure, obtaining a catalyst with formula 13 as a dark green solid (0.408 g, 57%).

$^1$H NMR (500 MHz, CD$_2$Cl$_2$): 17.75 (s, =CH, 1H), 7.28 (d, J=10.2 Hz, 1H), 7.16 (s, 1H), 7.11 (s, 1H) 6.94 (s, 1H), 6.80 (dd, J=9.0, 3.0 Hz, 1H), 6.41 (d, J=3.0 Hz, 1H), 6.19 (s, 1H), 4.24-4.16 (m, 1H), 4.11-4.02 (m, 1H), 4.02-3.92 (m, 1H), 3.92-3.81 (m, 1H), 2.97 (s, 6H, N(CH$_3$)$_2$), 2.63 (s, 3H), 2.42 (2s ovl, 6H), 2.40 (s, 3H), 2.17 (s, 3H), 1.60 (s, 3H).

$^{13}$C NMR (125 MHz, CD$_2$Cl$_2$): 280.9, 214.8, 152.5, 151.3, 140.6, 140.2, 138.5, 137.8, 136.9, 136.2, 135.5, 131.8, 131.0, 130.0, 129.7, 129.3, 128.5, 113.7, 114.4, 110.7, 51.9, 51.6, 40.6, 21.3, 20.9, 20.1, 19.1, 18.6, 17.2.

EXAMPLE X

The synthesis of a Catalyst with Formula 16 (in Accordance with Diagram II)

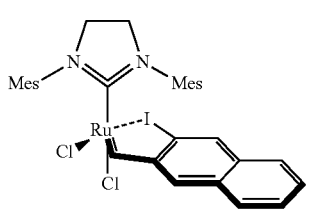

Formula 16

Procedure: using a protective atmosphere of argon, in a Schlenk flask are placed iodonaphthalene derivative with formula 27 (0.137 g, 0.466 mmol):

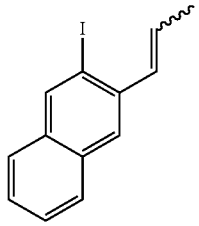

Formula 27 dry, deoxygenated toluene (6 ml), and a solid carbene ruthenium complex with formula 6b ('catalyst M31', Umicore AG & Co KG, 0.239 g, 0.316 mmol), in the sequence indicated. The suspension obtained is mixed at a temperature of 80° C. for 1 hour. From this moment, all operations are carried out in air, without the use of a protective atmosphere of argon. The reaction mixture is cooled to room temperature, diluted with n-pentane (1 ml), filtered using a Schott filter, rinsed with n-pentane (2×10 ml), and dried under pressure, obtaining a catalyst with formula 16 as a dark green solid (0.183 g, 78%).

$^1$H NMR (500 MHz, CD$_2$Cl$_2$): 18.08 (d, J=1.0 Hz, =CH, 1H), 8.12 (s, 1H), 8.00 (d, J=8.5 Hz, 1H), 7.77-7.70 (m, 2H), 7.56 (ddd, J=7.5, 6.0, 2.0 Hz, 1H), 7.42 (s, 1H), 7.17 (s, 1H), 7.06 (s, 1H), 6.95 (s, 1H), 5.59 (s, 1H), 4.25-4.18 (m, 1H), 4.11-3.95 (m, 2H), 3.91-3.84 (m, 1H), 2.70 (s, 3H), 2.50 (s, 3H), 2.44 (s, 3H), 2.39 (s, 3H), 1.88 (s, 3H), 1.63 (s, 3H).

$^{13}$C NMR (125 MHz, CD$_2$Cl$_2$): 280.6, 215.0, 154.7, 140.8, 140.5, 138.9, 138.2, 136.4, 136.1, 135.7, 134.2, 133.49, 133.47, 131.9, 131.2, 130.11, 130.10, 129.8, 129.0, 128.7, 128.4, 127.7, 126.5, 95.8, 51.9, 51.6, 21.4, 21.0, 20.4, 20.2, 18.9, 18.1.

EXAMPLE XI

Synthesis of a Catalyst with Formula 19 (in Accordance with Diagram II)

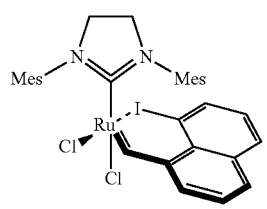

Formula 19

Procedure: using a protective atmosphere of argon, in the Schlenk flask are placed iodonaphthalene derivative with formula 30 (0.138 g, 0.469 mmol).

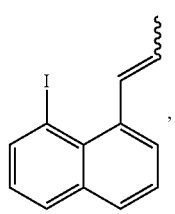

Formula 30 dry, deoxygenated toluene (6 ml), and solid carbene ruthenium complex with formula 6b ('catalyst M31', Umicore AG & Co KG, 0.237 mg, 0.313 mmol), in the sequence referred to. The suspension obtained is mixed at a temperature of 80° C. for 1 hour. From that moment, all subsequent operations are carried out in air, without the use of a protective atmosphere of argon. The reaction mixture is cooled to room temperature, diluted with n-pentane (6 ml), filtered using a Schott filter, rinsed with n-pentane (2×10 ml), and dried under pressure, obtaining a catalyst with formula 19, as a dark green solid (0.113 mg, 48%).

$^1$H NMR (500 MHz, CD$_2$Cl$_2$): 18.69 (s, 'CH, 1H), 7.99-7.94 (m ovl, 2H), 7.95 (d, J=7.5 Hz, 1H), 7.32-7.22 (m, 2H), 7.18 (dd, J=8.0, 8.0 Hz, 1H), 7.13 (s, 1H), 7.02 (s, 1H), 6.83 (s, 1H), 5.63 (s, 1H), 4.32-4.22 (m, 1H), 4.15-4.04 (m, 2H), 3.97-3.88 (m, 1H), 2.75 (s, 3H), 2.57 (s, 3H), 2.47 (s, 3H), 2.37 (s, 3H), 2.02 (s, 3H), 1.50 (s, 3H).

$^{13}$C NMR (125 MHz, CD$_2$Cl$_2$): 284.2, 216.3, 144.6, 140.7, 140.0, 138.6, 138.5, 138.1, 136.9, 136.3, 136.1, 135.7, 134.9, 133.0, 132.9, 132.4, 131.3, 131.2, 130.04, 130.00, 128.8, 127.4, 127.2, 87.6, 52.1, 51.5, 21.3, 21.1, 20.4 (ovl), 19.1, 18.0.

EXAMPLE XII

Testing the catalytic activity for cyclisation of diethyl diallylmalonate using H-NMR methods (in accordance with diagram III).

Diagram III

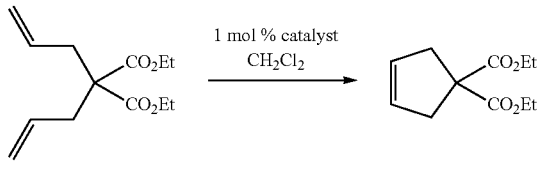

Solution A:
To the 5 ml measurement flask is added diethyl diallylmalonate (0.2882 g, 0.12 mmol), and CD$_2$Cl$_2$ is added up to the nominal value.

Solution B:
To a 1.5 ml vial is added a catalyst in accordance with the invention (12-19, 0.012 mmol), and 1 ml of CD$_2$Cl$_2$ is added.

Reaction Profile Measurements:
To an NMR tube is added 0.5 ml of solution A, and a micro-syringe is used to add 0.1 ml of solution B. The tube is closed with a cork, and, simultaneously, the time starts to be calculated and the content is mixed and placed in an NMR thermostatic device (at a temperature of 25° C., unless otherwise indicated), with successive $^1$H NMR spectra being recorded over a total period of 75 minutes. In an identical manner, the activity is studied of the commercially available catalysts 5a and 6a. On the basis of the integration of signals δ 2.6-2.9 ppm, conversions are determined, and the results are presented in FIG. 1, which shows progress during the course of the diethyl diallylmalonate cyclisation reaction in relation to various catalysts ($^1$H NMR).

On the basis of data obtained from tests of the catalytic activity of the complexes in accordance with the invention, it can be found that, at a temperature of 25° C., they are much more active than the commercially available catalyst of formula 6a.

EXAMPLE XIII

Test of the effect of temperature on the catalytic activity of complexes with formulae 15 and 18 in diethyl diallylmalonate cyclisation using $^1$H NMR methods (in accordance with Diagram III).

Figure 2:
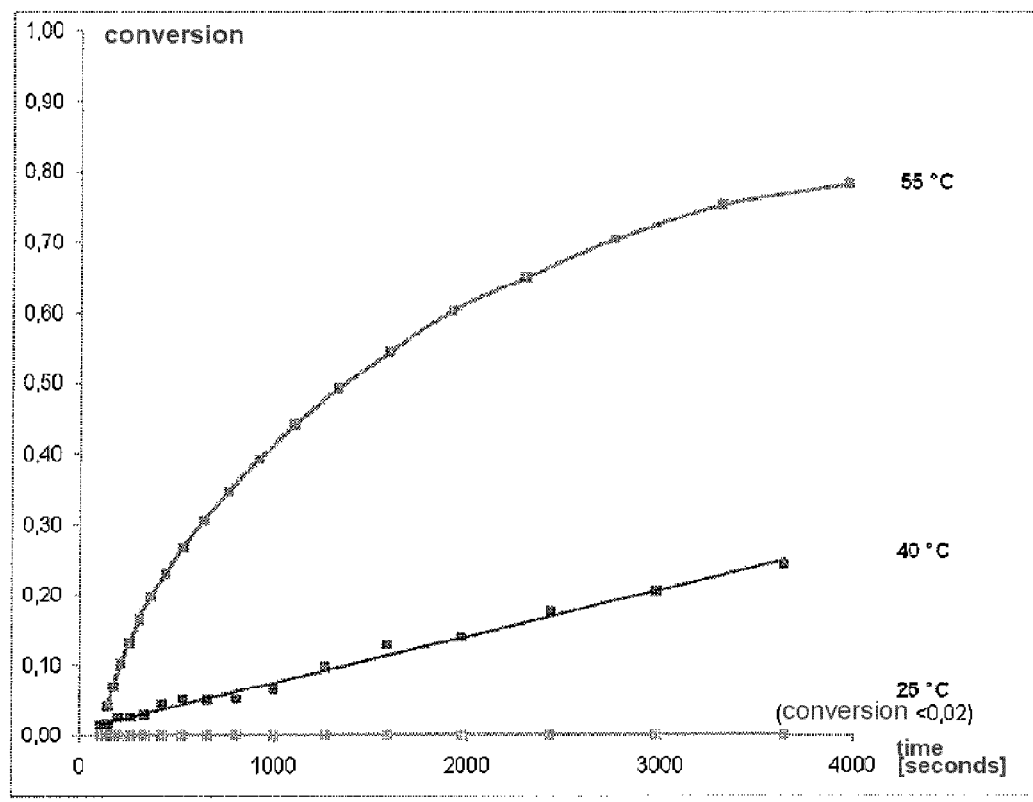
Figure 3:
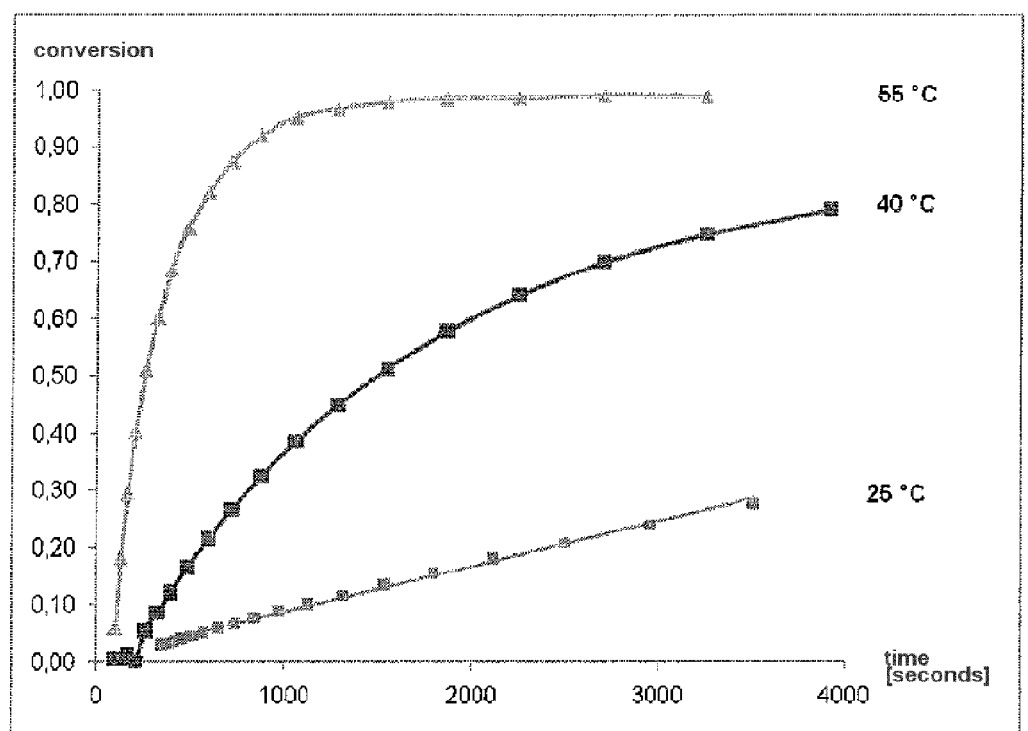

The test was carried out in accordance with the procedure described in example XII at temperatures of 25, 40, and 55° C. The reactions carried out at a temperature of 55° C. were carried out in an NMR Wilmad pressure tube. The results obtained are presented in FIG. 2 and FIG. 3, which show progress during the course of the diethyl diallylmalonate cyclisation reaction at various temperatures (by $^1$H NMR).

The results obtained show that the catalysts in accordance with the invention show thermal stability (and can also act at an elevated temperature), and, thanks to changes in activity as a function of temperature, the course of catalytic processes can be easily controlled.

EXAMPLE XIV

Examples of Application

Tests were carried out into catalytic activity with various substrates in accordance with Diagrams IV-X (the results are shown in tables 1-7 respectively).

Diagram IV

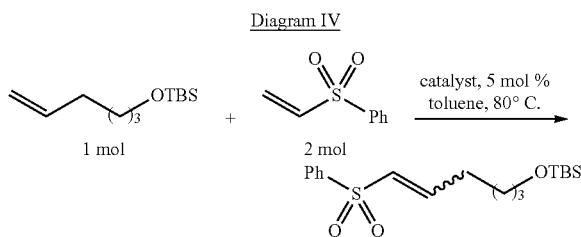

TABLE 1

Results of reactions on a model substrate in accordance with Diagram IV

| Catalyst | Duration of the reaction | Product yield |
|---|---|---|
| 15 | 30 minutes | 78% |
| 12 | 16 hours | 74% |
| 14 | 16 hours | 83% |

Diagram V

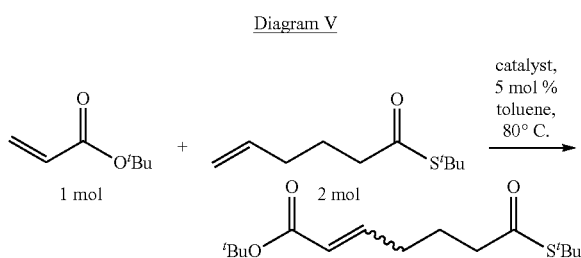

TABLE 2

Results of reactions on a model substrate in accordance with Diagram V

| Catalyst | Duration of the reaction | Product yield |
|---|---|---|
| 15 | 6 hours | 80% |
| 12 | 12 hours | 68% |
| 14 | 8 hours | 84% |

Diagram VI

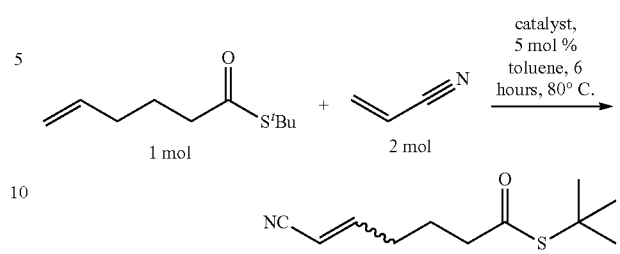

TABLE 3

Results of reactions on a model substrate in accordance with Diagram VI

| Catalyst | Product yield |
|---|---|
| 15 | 72% |
| 12 | 69% |
| 14 | 70% |
| 6A (known from the state of the art) | 22% |

Diagram VII

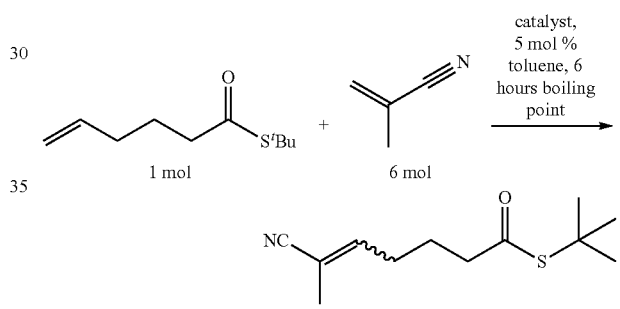

TABLE 4

Results of reactions on a model substrate in accordance with Diagram VII

| Catalyst | Product yield |
|---|---|
| 15 | 41% (23% at 80° C.) |
| 12 | 48% |
| 14 | 38% |
| 6A (known from the state of the art) | 11% |

Diagram VIII

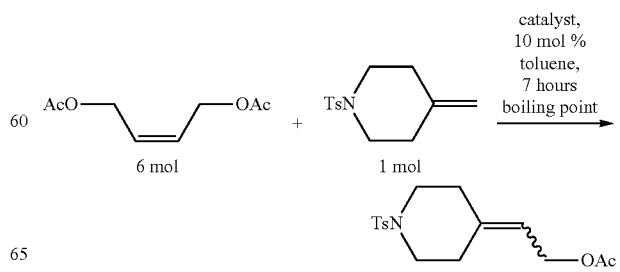

TABLE 5

Results of reactions on a model substrate in accordance with Diagram VIII

| Catalyst | Product yield |
|---|---|
| 15 | 62% |
| 12 | 45% |
| 14 | 63% |

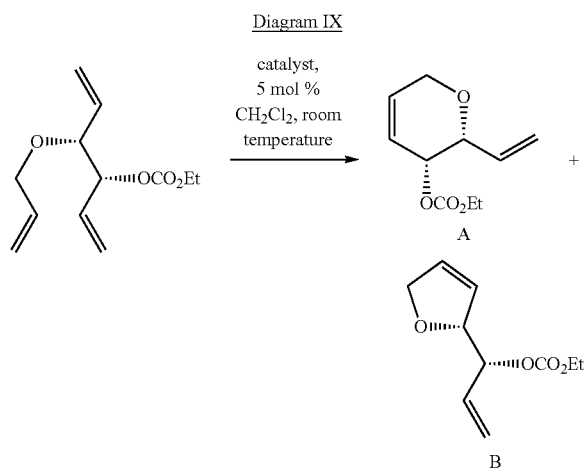

Diagram IX

TABLE 6

Results of reactions on a model substrate in accordance with Diagram IX

| Catalyst | Product yield | Proportions of isomers A:B |
|---|---|---|
| 12 | 88% | 2:1 |
| 14 | 74% | 3:1 |

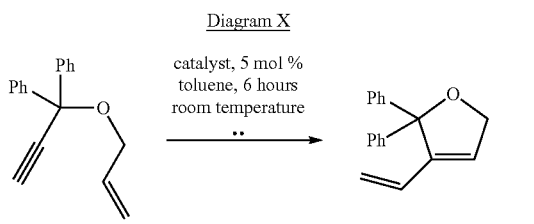 [SMILES: C#CC(OCC=C)(c1ccccc1)c1ccccc1 ; C=CC1=CCOC1(c1ccccc1)c1ccccc1]

Diagram X

TABLE 7

Results of reactions on a model substrate in accordance with Diagram X

| Catalyst | Duration of reaction | Product yield |
|---|---|---|
| 15 | 2.5 hours | 56% |
| 12 | 20 minutes | 97% |
| 14 | 20 minutes | 93% |
| 6a (known from the state of the art) | 12 hours | 92% |

The results presented in tables 3, 4, and 7 show clearly that the complexes in accordance with the invention are much more active than the catalyst 6a, which is known from the state of the art.

EXAMPLE XV

An example of the application of new ruthenium complexes in accordance with the invention as ROMP-type (ring-opening metathesis polymerisation-type) polymerisation catalysts.

Obtaining the Polydicyclopentadiene:

To the flask is added dicyclopentadiene (0.132 g, 1.0 mmol) in $CH_2Cl_2$ (5 ml), and mixing takes place at room temperature. Then, solution is added of the catalyst with formula 14 (0.0000025 g, 0.0003 mol %), and the contents of the flask are mixed at the same temperature for 1 minute. The contents of the flask are poured into another vessel containing 15 ml of methyl alcohol, and a solid precipitates, which is separated by filtration and dried at reduced pressure with the use of a pressure pump. Polydicyclopentadiene is obtained as an elastic white solid.

This example demonstrates that complexes in accordance with the invention may successfully be applied in a ROMP-type polymerisation reaction.

On the basis of the examples of embodiment presented above, it can be found that ruthenium complexes in accordance with the invention show high catalytic activity in comparison with complexes known from the state of the art. In addition, complexes in accordance with the invention are stable at an elevated temperature and may be stored without a protective gas atmosphere.

EXAMPLE XVI

Synthesis of a Catalyst with Formula 31 (in Accordance with Diagram II)

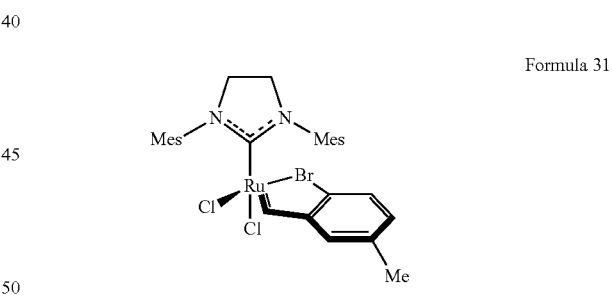

Formula 31

Procedure: using a protective atmosphere of argon, the styrene derivative 1-bromo-2-(1-propenyl)-4-methyl-benzene (254 mg, 1.2 mmol) and the solid carbene ruthenium complex with formula 6b ('catalyst M31', Umicore AG & Co KG; 749 mg, 1 mmol) are combined in a Schlenk flask and 20 ml of dry, deoxygenated toluene is added. The suspension obtained is stirred at a temperature of 80° C. for 15 minutes under argon. In the course of the reaction, the M31 complex dissolves within 3-5 minutes, while in 5-10 minutes a green precipitate is observed. The reaction mixture is cooled to room temperature, filtered on a Schott filter, washed with toluene and dried under vacuum obtaining catalyst with formula 31 as green powder (89 mg, 0.13 mmol, 13%).

$^1$H NMR (500 MHz, $CD_2Cl_2$): 17.75 (d, J=1.0 Hz, Ru=CH, 1H), 7.40 (d, J=8.0 Hz, 1H), 7.32 (dd, J=0.5, 8.0 Hz, 1H), 7.16 (s, 1H), 7.11 (s, 1H), 6.98 (s, 1H), 6.86 (d, J=0.5 Hz,

1H), 6.11 (s, 1H), 4.24-4.15 (m, 1H), 4.11-4.02 (m, 1H), 4.01-3.92 (m, 1H), 3.90-3.82 (m, 1H), 2.62 (s, 3H), 2.45 (s, 3H), 2.44 (s, 3H), 2.42 (s, 3H), 2.40 (s, 3H), 2.22 (s, 3H), 1.54 (s, 3H).

$^{13}$C NMR (125 MHz, CD$_2$Cl$_2$): 279.0, 214.5, 151.8, 140.8, 140.3, 139.8, 138.9, 138.0, 136.9, 136.1, 135.5, 131.7, 131.2, 131.0, 130.1, 129.7, 129.2, 128.5, 127.3, 123.0, 51.9, 51.6, 21.4, 21.2, 20.9, 20.2, 19.2, 18.6, 17.2.

Trace signals of the solvent (toluene) were not listed.

EXAMPLE XVII

Synthesis of a Catalyst with Formula 32 (in Accordance with Diagram II)

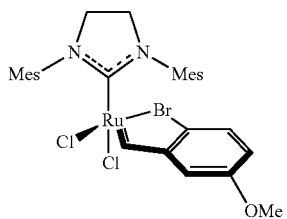

Formula 32

Procedure: using a protective atmosphere of argon, the styrene derivative 1-bromo-2-(1-propenyl)-4-methoxy-benzene (545 mg, 2.4 mmol) and the solid carbene ruthenium complex with formula 6b ('catalyst M31', Umicore AG & Co KG; 1497 mg, 2 mmol) are combined in a Schlenk flask and 40 ml of dry, deoxygenated toluene is added. The suspension obtained is stirred at a temperature of 80° C. for 15 minutes under argon. In the course of the reaction, the M31 complex dissolves within 3-5 minutes, while in 5-10 minutes a green precipitate is observed. The reaction mixture is cooled to room temperature, filtered on a Schott filter, washed with toluene and dried under vacuum obtaining a catalyst with formula 32, as a green powder (396 mg, 0.58 mmol, 29%).

$^1$H NMR (500 MHz, CD$_2$Cl$_2$): 17.76 (d, J=1.0 Hz, Ru=CH, 1H), 7.40 (dd, J=1.0, 6.7 Hz, 1H), 7.16 (s, 1H), 7.12 (s, 1H), 7.06 (dd, J=3.0, 8.6Hz, 1H), 6.96 (s, 1H), 6.60 (d, J=3.0 Hz, 1H), 6.15 (s, 1H), 4.25-4.15 (m, 1H), 4.11-4.04 (m, 1H), 4.01-3.94 (m, 1H), 3.90-3.83 (m, 1H), 3.81 (s, OCH3, 3H), 2.61 (s, 3H), 2.43 (s, 3H), 2.42 (s, 3H), 2.40 (s, 3H), 2.20 (s, 3H), 1.60 (s, 3H).

$^{13}$C NMR (125 MHz, CD$_2$Cl$_2$): 278.2, 214.3, 160.9, 152.7, 140.8, 140.3, 138.9, 137.9, 136.8, 136.0, 135.4, 131.6, 131.0, 130.1, 129.7, 129.2, 129.0, 116.2, 116.0, 111.5, 56.2, 51.9, 51.6, 21.3, 20.9, 20.2, 19.1, 18.5, 17.3.

Trace signals of the solvent (toluene) were not listed.

The invention claimed is:

1. A complex of ruthenium with formula 1,

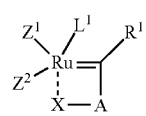

formula 1 wherein

L$^1$ denotes an inert ligand;
Z$^1$ and Z$^2$ denote, independently, an anion ligand;
X denotes a halogen atom;

R$^1$ denotes an atom of hydrogen, a halogen atom, C$_1$-C$_{12}$ alkyl, C$_3$-C$_{12}$ cycloalkyl, C$_2$-C$_{12}$ alkenyl, C$_3$-C$_{12}$ cycloalkenyl, C$_2$-C$_{12}$ alkynyl, C$_1$-C$_{12}$ alkoxyl, C$_5$-C$_{20}$ aryl, C$_5$-C$_{20}$ heteroaryl, or 3-12-membered heterocycle;

A denotes a bivalent radical selected from the group consisting of C$_1$-C$_{12}$ alkylene, C$_2$-C$_{12}$ alkenylene, C$_2$-C$_{12}$ alkynylene, C$_5$-C$_{20}$ arylene, and C$_5$-C$_{20}$ heteroarylene, wherein the C$_1$-C$_{12}$ alkylene, the C$_2$-C$_{12}$ alkenylene, the C$_2$-C$_{12}$ alkynylene, the C$_5$-C$_{20}$ arylene, and the C$_5$-C$_{20}$ heteroarylene may be optionally substituted with at least one functional group R$^2$;

each R$^2$ functional group denotes, independently, a halogen atom, C$_1$-C$_{12}$ alkyl, C$_2$-C$_{12}$ alkenyl, C$_2$-C$_{12}$ alkynyl, —OR$^3$, —SR$^3$, —S(O)$_m$R$^3$, —SO$_2$NR$^3$R$^4$, —S(O)$_2$OR$^3$, —NO$_2$, —NO, —SCN, —NR$^3$R$^4$, —CN, —C(O)R$^3$, —OC(O)R$^3$, —O(CR$^3$R$^4$)$_n$R$^5$, —NR$^3$C(O)R$^4$, —(CR$^3$R$^4$)$_n$C(O)OR$^5$, —(CR$^3$R$^4$)$_n$OR$^5$, —C(=NR$^3$)NR$^4$R$^5$, —NR$^3$C(O)NR$^4$R$^5$, —NR$^3$S(O)$_p$R$^4$, —NC(=O)R$^3$C(=O)R$^4$, —NR$^3$P(=O)R$^4$R$^5$, —NR$^3$As(=O)R$^4$R$^5$, —PR$^3$R$^4$, —POR$^3$R$^4$, —POR$^3$OR$^4$, —P(=O)R$^3$R$^4$, —P(=O)OR$^3$R$^4$, —P(=O)OR$^3$OR$^4$, —AsR$^3$R$^4$, —AsOR$^3$R$^4$, —AsOR$^3$OR$^4$, —As(=O)R$^3$R$^4$, —As(=O)OR$^3$R$^4$, —As(=O)OR$^3$OR$^4$, —NR$^3$—C(=NR$^4$)NR$^5$R$^6$, —C(=O)R$^3$, —C(=O)OR$^3$, —C(=S)OR$^3$, —C(=O)SR$^3$, —C(=S)SR$^3$, —C(=S)NR$^3$R$^4$, —SiR$^3$R$^4$R$^5$, —SiOR$^3$R$^4$R$^5$, —SiOR$^3$OR$^4$R$^5$, —SiOR$^3$OR$^4$OR$^5$, —(CR$^3$R$^4$)$_n$(3-12-membered heterocycle), —(CR$^3$R$^4$)$_n$(C$_3$-C$_{12}$ cycloalkyl), —(CR$^3$R$^4$)$_n$(C$_5$-C$_{20}$ aryl), —(CR$^3$R$^4$)$_n$(5-12-membered heteroaryl), —(CR$^3$R$^4$)$_n$C(O)NR$^5$R$^6$, or —(CR$^3$R$^4$)$_n$C(O)R$^5$; and/or R$^2$ groups with adjacent atoms may bond together, creating C$_5$-C$_{20}$ aryl or 3-12-membered heterocycle; and/or R$^2$ groups with adjacent atoms may bond with the R$^1$ group, creating C$_5$-C$_{20}$ aryl, indenylene, heteroindenylene, 3-12-membered heterocycle, and polycyclic or heteropolycyclic arrangements, wherein the C$_5$-C$_{20}$ aryl, indenylene, heteroindenylene, 3-12-membered heterocycle, and polycyclic or heteropolycyclic arrangements may be substituted with at least one functional group selected from the group consisting of a halogen atom, C$_1$-C$_{12}$ alkyl, C$_2$-C$_{12}$ alkenyl, C$_2$-C$_{12}$ alkynyl, —OR$^3$, —SR$^3$, —S(O)$_m$R$^3$, —SO$_2$NR$^3$R$^4$, —S(O)$_2$OR$^3$, —NO$_2$, —NO, —SCN, —NR$^3$R$^4$, —CN, —C(O)R$^3$, —OC(O)R$^3$, —O(CR$^3$R$^4$)$_n$R$^5$, —NR$^3$C(O)R$^4$, —(CR$^3$R$^4$)$_n$C(O)OR$^5$, —(CR$^3$R$^4$)$_n$OR$^5$, —C(=NR$^3$)NR$^4$5$^4$, —NR$^3$C(O)NR$^4$R$^5$, —NR$^3$S(O)$_p$R$^4$, —NC(=O)R$^3$C(=O)R$^4$, —NR$^3$P(=O)R$^4$R$^5$, —NR$^3$As(=O)R$^4$R$^5$, —PR$^3$R$^4$, —POR$^3$R$^4$, —POR$^3$OR$^4$, —P(=O)R$^3$R$^4$, —P(=O)OR$^3$R$^4$, —P(=O)OR$^3$OR$^4$, —AsR$^3$R$^4$, —AsOR$^3$R$^4$, —AsOR$^3$OR$^4$, —As(=O)R$^3$R$^4$, —As(=O)OR$^3$R$^4$, —As(=O)OR$^3$OR$^4$, —NR$^3$—C(=NR$^4$)NR$^5$R$^6$, —C(=O)R$^3$, —C(=O)OR$^3$, —C(=S)OR$^3$, —C(=O)SR$^3$, —C(=S)SR$^3$, —C(=S)NR$^3$R$^4$, —SiR$^3$R$^4$R$^5$, —SiOR$^3$R$^4$R$^5$, —SiOR$^3$OR$^4$R$^5$, —SiOR$^3$OR$^4$OR$^5$, —(CR$^3$R$^4$)$_n$(3-12-membered heterocycle), —(CR$^3$R$^4$)$_n$(C$_3$-C$_{12}$ cycloalkyl), —(CR$^3$R$^4$)$_n$(C$_5$-C$_{20}$ aryl), —(CR$^3$R$^4$)$_n$(5-12-membered heteroaryl), —(CR$^3$R$^4$)$_n$C(O)NR$^5$R$^6$, and —(CR$^3$R$^4$)$_n$C(O)R$^5$;

each functional group R$^3$, R$^4$, R$^5$, and R$^6$ denotes, independently, an atom of hydrogen, a halogen atom, C$_1$-C$_{12}$ alkyl, C$_2$-C$_{12}$ alkenyl, C$_2$-C$_{12}$ alkynyl, C$_3$-C$_{12}$ cycloalkyl, C$_5$-C$_{20}$ aryl, or 5-12-membered heterocycle;

each m denotes, independently, 0, 1, or 2;
each n denotes, independently, 0, 1, 2, 3, or 4; and
each p denotes, independently, 1 or 2.

2. The complex according to claim 1, wherein anion ligands $Z^1$ and $Z^2$ denote, independently, a halogen atom, the group —CN, —SCN, —OR$^{13}$, —SR$^{13}$, —O(C═O)R$^{13}$, —O(SO$_2$)R$^{13}$, —OSiR$_3^{13}$, wherein R$^{13}$ denotes C$_1$-C$_{12}$ alkyl, C$_3$-C$_{12}$ cycloalkyl, C$_2$-C$_{12}$ alkenyl, or C$_5$-C$_{20}$ aryl, which may be optionally substituted with at least one C$_1$-C$_{12}$ alkyl, C$_1$-C$_{12}$ perhalogenalkyl, C$_1$-C$_{12}$ alkoxyl, or a halogen atom; and R$^1$ denotes an atom of hydrogen, the inert ligand L$^1$ is selected from the group consisting of —P(R$^7$)$_3$, —P(OR$^7$)$_3$, and a N-heterocyclic carbene ligand with formula 7a, 7b, 7c, 7d, 7e, 7f, 7g, 7h, 7i, 7j, 7k, 7l, 7m, 7n, 7o, or 7p:

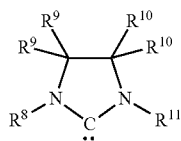

formula 7a

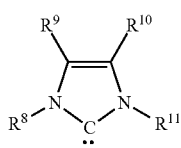

formula 7b

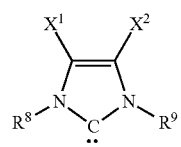

formula 7c

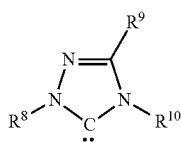

formula 7d

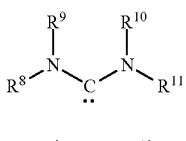

formula 7e

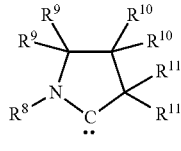

formula 7f

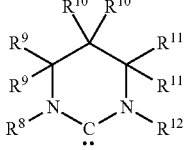

formula 7g

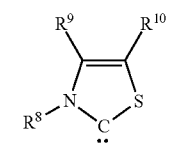

formula 7h

-continued

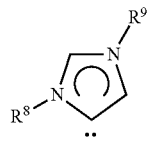

formula 7i

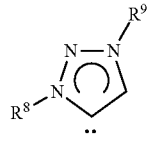

formula 7j

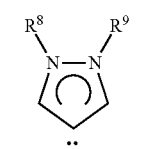

formula 7k

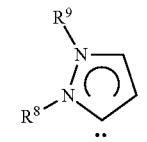

formula 7l

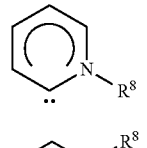

formula 7m

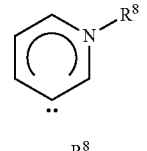

formula 7n

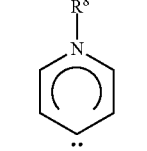

formula 7o formula 7p wherein
each R$^7$ denotes, independently, C$_1$-C$_{12}$ alkyl, C$_3$-C$_{12}$ cycloalkyl, C$_5$-C$_{20}$ aryl, or 5-12-membered heteroaryl; each R$^8$, R$^9$, R$^{10}$, R$^{11}$, and R$^{12}$ denote, independently, an atom of hydrogen, C$_1$-C$_{12}$ alkyl, C$_3$-C$_{12}$ cycloalkyl, C$_2$-C$_{12}$ alkenyl, or C$_5$-C$_{20}$ aryl, which may be optionally substituted with at least one C$_1$-C$_{12}$ alkyl, C$_1$-C$_{12}$ perhalogenalkyl, C$_1$-C$_{12}$ alkoxyl, or a halogen atom, and the groups R$^8$, R$^9$, R$^{10}$, R$^{11}$, and R$^{12}$ may optionally bond with each other, and X$^1$ and X$^2$ denote, independently, a halogen atom.

3. The complex according to claim 1, wherein
$Z^1$ and $Z^2$ each denote an atom of chlorine;
X denotes an atom of bromine or iodine; and
R$_1$ denotes an atom of hydrogen, A denotes -1,2-phenylene, -1,2-naphthylene, -2,3-naphthylene or -1,8-naphthylene, which may be substituted with at least one functional group selected from the group consisting of and —$NO_2$ and —$NMe_2$; and the inert ligand $L^1$ denotes a ligand with formula 7a or 7b;

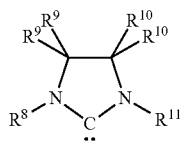

formula 7a

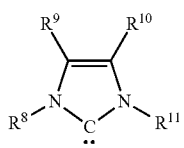

formula 7b wherein the functional groups $R^8$, $R^9$, $R^{10}$, and $R^{11}$ denote, independently, an atom of hydrogen, $C_1$-$C_{12}$ alkyl, $C_3$-$C_{12}$ cycloalkyl, $C_2$-$C_{12}$ alkenyl, or $C_5$-$C_{20}$ aryl, which may be optionally substituted with at least one $C_1$-$C_{12}$ alkyl, $C_1$-$C_{12}$ perhalogenalkyl, $C_1$-$C_{12}$ alkoxyl, or a halogen atom, and the groups $R^8$, $R^9$, $R^{10}$, and $R^{11}$ may optionally bond with each other.

4. The complex according to claim 1, wherein $Z^1$ and $Z^2$ each denote an atom of chlorine;

X denotes an atom of bromine or iodine; and $R_1$ denotes an atom of hydrogen,

A denotes -1,2-phenylene, -1,2-naphthylene, -2,3-naphthylene or -1,8-naphthylene, which may be substituted with at least one functional group selected from the group consisting of -OMe and -Me; and the inert ligand $L^1$ denotes a ligand with formula 7a or 7b;

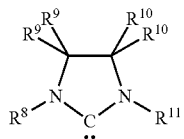

formula 7a

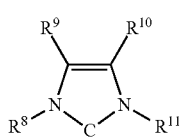

formula 7b wherein the functional groups $R^8$, $R^9$, $R^{10}$, and $R^{11}$ denote, independently, an atom of hydrogen, $C_1$-$C_{12}$ alkyl, $C_3$-$C_{12}$ cycloalkyl, $C_2$-$C_{12}$ alkenyl, or $C_5$-$C_{20}$ aryl, which may be optionally substituted with at least one $C_1$-$C_{12}$ alkyl, $C_1$-$C_{12}$ perhalogenalkyl, $C_1$-$C_{12}$ alkoxyl, or a halogen atom, and the groups $R^8$, $R^9$, $R^{10}$, and $R^{11}$ may optionally bond with each other.

5. The complex of claim 1, wherein the complex comprises formula 12, 14, 15, 17, 18, 13, 16, 19, 31, or 32:

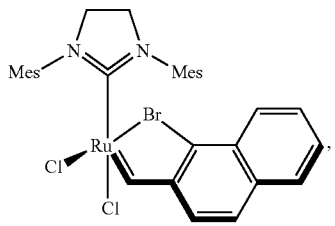

Formula 12

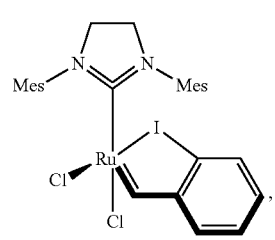

Formula 14

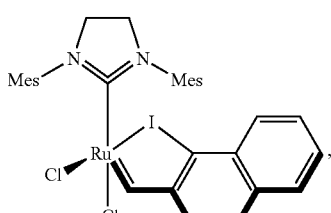

Formula 15

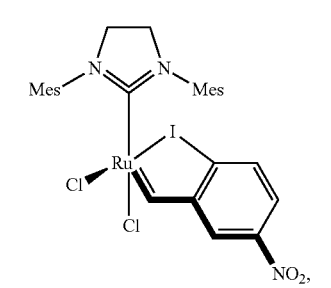

Formula 17

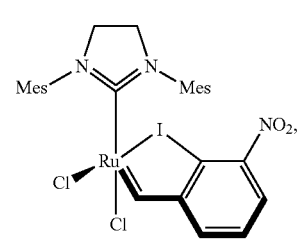

Formula 18

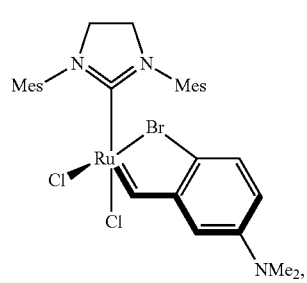

formula 13

-continued

Formula 16

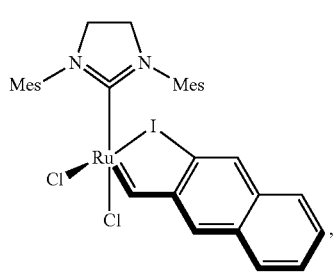,

Formula 19

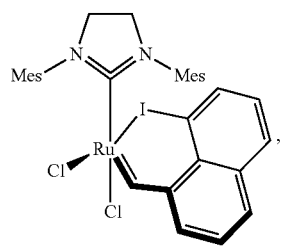,

Formula 31

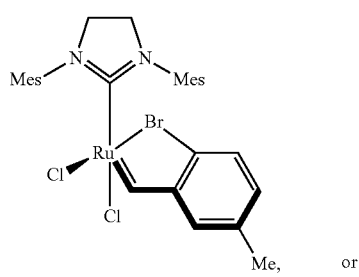, or

Formula 32

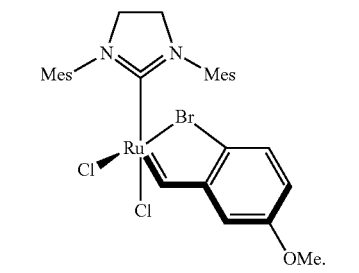.

6. A method of producing the ruthenium complex according to claim 1, comprising reacting the compound of formula 9

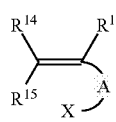

formula 9 wherein $R^{14}$ and $R^{15}$ denote, independently, an atom of hydrogen or the alkyl group $C_1$-$C_{12}$;

$R^1$ denotes hydrogen, a halogen atom, $C_1$-$C_{12}$ alkyl, $C_3$-$C_{12}$ cycloalkyl, $C_2$-$C_{12}$ alkenyl, $C_3$-$C_{12}$ cycloalkenyl, $C_2$-$C_{12}$ alkynyl, $C_3$-$C_{12}$ cycloalkynyl, $C_1$-$C_{12}$ alkoxyl, $C_5$-$C_{20}$ aryl, $C_5$-$C_{20}$ heteroaryl, or 3-12-membered heterocycle;

X denotes a halogen atom;

A denotes a bivalent radical selected from the group comprising consisting of $C_1$-$C_{12}$ alkylene, $C_2$-$C_{12}$ alkenylene, $C_2$-$C_{12}$ alkynylene, $C_5$-$C_{20}$ arylene, and $C_5$-$C_{20}$ heteroarylene, wherein the $C_1$-$C_{12}$ alkylene, the $C_2$-$C_{12}$ alkenylene, the $C_2$-$C_{12}$ alkynylene, the $C_5$-$C_{20}$ arylene, and the $C_5$-$C_{20}$ heteroarylene may be optionally substituted with at least one functional group $R^2$;

wherein each $R^2$ functional group denotes, independently, a halogen atom, $C_1$-$C_{12}$ alkyl, $C_2$-$C_{12}$ alkenyl, $C_2$-$C_{12}$ alkynyl, —$OR^3$, —$SR^3$, —$S(O)_mR^3$, —$SO_2NR^3R^4$, —$S(O)_2OR^3$, —$NO_2$, —NO, —SCN, —$NR^3R^4$, —CN, —$C(O)R^3$, —$OC(O)R^3$, —$O(CR^3R^4)_nR^5$, —$NR^3C(O)R^4$, —$(CR^3R^4)_nC(O)OR^5$, —$(CR^3R^4)_nOR^5$, —$C(=NR^3)NR^4 5^4$, —$NR^3C(O)NR^4R^5$, —$NR^3S(O)_pR^4$, —$NC(=O)R^3C(=O)R^4$, —$NR^3P(=O)R^4R^5$, —$NR^3As(=O)R^4R^5$, —$PR^3R^4$, —$POR^3R^4$, —$POR^3OR^4$, —$P(=O)R^3R^4$, —$P(=O)OR^3R^4$, —$P(=O)OR^3OR^4$, —$AsR^3R^4$, —$AsOR^3R^4$, —$AsOR^3OR^4$, —$As(=O)R^3R^4$, —$As(=O)OR^3R^4$, —$As(=O)OR^3OR^4$, —$NR^3$—$C(=NR^4)NR^5R^6$, —$C(=O)R^3$, —$C(=O)OR^3$, —$C(=S)OR^3$, —$C(=O)SR^3$, —$C(=S)SR^3$, —$C(=S)NR^3R^4$, —$SiR^3R^4R^5$, —$SiOR^3R^4R^5$, —$SiOR^3OR^4R^5$, —$SiOR^3OR^4OR^5$, —$(CR^3R^4)_n$(3-12-membered heterocycle), —$(CR^3R^4)_n$($C_3$-$C_{12}$ cycloalkyl), —$(CR^3R^4)_n$($C_5$-$C_{20}$ aryl), —$(CR^3R^4)_n$(5-12-membered heteroaryl), —$(CR^3R^4)_nC(O)NR^5R^6$, or —$(CR^3R^4)_nC(O)R^5$;

and/or $R^2$ groups with adjacent atoms may bond together, creating $C_5$-$C_{20}$ aryl or 3-12-membered heterocycle;

and/or $R^2$ groups with adjacent atoms may bond with the $R^1$ group, creating $C_5$-$C_{20}$ aryl, indenylene, heteroindenylene, 3-12-membered heterocycle, and polycyclic or heteropolycyclic arrangements, wherein the $C_5$-$C_{20}$ aryl, indenylene, heteroindenylene, 3-12-membered heterocycle, and polycyclic or heteropolycyclic arrangements may be substituted with at least one functional group selected from the group consisting of a halogen atom, $C_1$-$C_{12}$ alkyl, $C_2$-$C_{12}$ alkenyl, $C_2$-$C_{12}$ alkynyl, —$OR^3$, —$SR^3$, —$S(O)_mR^3$, —$SO_2NR^3R^4$, —$S(O)_2OR^3$, —$NO_2$, —NO, —SCN, —$NR^3R^4$, —CN, —$C(O)R^3$, —$OC(O)R^3$, —$O(CR^3R^4)_nR^5$, —$NR^3C(O)R^4$, —$(CR^3R^4)_nC(O)OR^5$, —$(CR^3R^4)_nOR^5$, —$C(=NR^3)NR^4R^5$, —$NR^3C(O)NR^4R^5$, —$NR^3S(O)_pR^4$, —$NC(=O)R^3C(=O)R^4$, —$NR^3P(=O)R^4R^5$, —$NR^3As(=O)R^4R^5$, —$PR^3R^4$, —$POR^3R^4$, —$POR^3OR^4$, —$P(=O)R^3R^4$, —$P(=O)OR^3R^4$, —$P(=O)OR^3OR^4$, —$AsR^3R^4$, —$AsOR^3R^4$, —$AsOR^3OR^4$, —$As(=O)R^3R^4$, —$As(=O)OR^3R^4$, —$As(=O)OR^3OR^4$, —$NR^3$—$C(=NR^4)NR^5R^6$, —$C(=O)R^3$, —$C(=O)OR^3$, —$C(=S)OR^3$, —$C(=O)SR^3$, —$C(=S)SR^3$, —$C(=S)NR^3R^4$, —$SiR^3R^4R^5$, —$SiOR^3R^4R^5$, —$SiOR^3OR^4R^5$, —$SiOR^3OR^4OR^5$, —$(CR^3R^4)_n$(3-12-membered heterocycle), —$(CR^3R^4)_n$($C_3$-$C_{12}$ cycloalkyl), —$(CR^3R^4)_n$($C_5$-$C_{20}$ aryl), —$(CR^3R^4)_n$(5-12-membered heteroaryl), —$(CR^3R^4)_nC(O)NR^5R^6$, and —$(CR^3R^4)_nC(O)R^5$;

each functional group $R^3$, $R^4$, $R^5$, and $R^6$ denotes, independently, an atom of hydrogen, a halogen atom, $C_1$-$C_{12}$ alkyl, $C_2$-$C_{12}$ alkenyl, $C_2$-$C_{12}$ alkynyl, $C_3$-$C_{12}$ cycloalkyl, $C_5$-$C_{20}$ aryl, or 5-12-membered heterocycle;

each m denotes, independently, 0, 1, or 2;

each n denotes, independently, 0, 1, 2, 3, or 4;

each p denotes, independently, 1 or 2;

with a carbene ruthenium complex with formula 11a, 11b, 11c, or 11d:

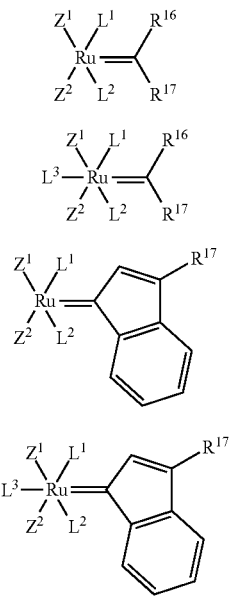

formula 11a formula 11b formula 11c formula 11d wherein
L$^1$, L$^2$, and L$^3$ denote, independently, an inert ligand;
Z$^1$ and Z$^2$ denote, independently, an anion ligand;
R$^{16}$ has the same meaning as R$^1$ in formula 9; and R$^{17}$ denotes an atom of hydrogen, C$_5$-C$_{20}$ aryl, C$_5$-C$_{20}$ heteroaryl, vinyl, or allenyl.

7. The method according to claim 6, wherein the reaction is carried out in the presence of anhydrous halogen salts of copper(I) in the presence of Brønsted acids, in a solvent.

8. The method according to claim 7, wherein the anhydrous halogen salts of copper (I) Are CuBr or CuCl.

9. Method The method according to claim 6, wherein the reaction is carried out at a temperature in the range of 0-120° C.

10. The method according to claim 7, wherein the Brønsted acids comprise H$_2$SO$_4$, HCl, HNO$_3$, H$_3$PO$_4$, sulphonated polymers (Nafion-H), or other acids bonded with a fixed sudstrate.

11. The method according to claim 6, wherein the reaction is carried out in a protic or aprotic solvent or a chlorinated solvent or in anaromatic hydrocarbon solvent, or in mixtures thereof.

12. The method according to claim 6, wherein the reaction is carried out in a solvent.

13. The method according to claim 12, wherein the solvent is methylene chloride, toluene, Or mixture thereof.

14. A method comprising introducing the ruthenium complexes of claim 1 as (pre)catalysts in metathes is processes.

15. The method according to claim 14, wherein the metathesis processes comprise ring-opening metathesis reactions, homometathesis, cross-metathesis, metathesis of the alkene-alkyne (ene-yne) type, ring-closing metathesis or ROMP-type polymerisation reactions.

* * * * *